US011672771B2

(12) United States Patent
Taub et al.

(10) Patent No.: US 11,672,771 B2
(45) Date of Patent: Jun. 13, 2023

(54) BETA-ALETHINE, IMMUNE MODULATORS, AND USES THEREOF

(71) Applicants: AxImmune, Inc., Aurora, CO (US); Colorado State University Research Foundation, Fort Collins, CO (US)

(72) Inventors: Floyd Taub, Golden, CO (US); Amanda Guth, Fort Collins, CO (US)

(73) Assignees: AxImmune, Inc., Aurora, CO (US); Colorado State University Research Foundation, Fort Collins, CO (US)

(*) Notice: Subject to any disclaimer, the term of this patent is extended or adjusted under 35 U.S.C. 154(b) by 95 days.

(21) Appl. No.: 16/347,005

(22) PCT Filed: Nov. 3, 2017

(86) PCT No.: PCT/US2017/060005
§ 371 (c)(1),
(2) Date: May 2, 2019

(87) PCT Pub. No.: WO2018/085698
PCT Pub. Date: May 11, 2018

(65) Prior Publication Data
US 2020/0069616 A1 Mar. 5, 2020

Related U.S. Application Data

(60) Provisional application No. 62/470,571, filed on Mar. 13, 2017, provisional application No. 62/449,090, filed on Jan. 22, 2017, provisional application No. 62/439,024, filed on Dec. 24, 2016, provisional application No. 62/432,663, filed on Dec. 11, 2016, provisional application No. 62/417,992, filed on Nov. 4, 2016.

(51) Int. Cl.
*A61K 31/16* (2006.01)
*A61P 35/00* (2006.01)
*A61K 9/00* (2006.01)
*A61K 38/17* (2006.01)
*A61K 38/20* (2006.01)
*A61K 39/395* (2006.01)
*C12Q 1/6886* (2018.01)

(52) U.S. Cl.
CPC ............ *A61K 31/16* (2013.01); *A61K 9/0019* (2013.01); *A61K 38/177* (2013.01); *A61K 38/2013* (2013.01); *A61K 39/3955* (2013.01); *A61P 35/00* (2018.01); *C12Q 1/6886* (2013.01); *C12Q 2600/106* (2013.01); *C12Q 2600/158* (2013.01)

(58) Field of Classification Search
CPC ......... A61K 38/10; A61K 38/17; A61K 35/15
See application file for complete search history.

(56) References Cited

U.S. PATENT DOCUMENTS

| 6,046,241 A * | 4/2000 | Knight .................. A61K 31/16 |
| | | 424/277.1 |
| 2004/0110680 A1 | 6/2004 | Knight et al. |
| 2005/0227929 A1 | 10/2005 | Masferrer |
| 2016/0317615 A1 | 11/2016 | Gonzalez et al. |

FOREIGN PATENT DOCUMENTS

| WO | 2001/002013 A1 | 1/2011 | |
| WO | WO-2013173223 A1 * | 11/2013 | .............. A61P 43/00 |
| WO | 2015/061752 A1 | 4/2015 | |
| WO | 2016/100619 A2 | 6/2016 | |
| WO | 2016/161347 A1 | 10/2016 | |

OTHER PUBLICATIONS

Melero et al., Evolving synergistic combinations of targeted immunotherapies to combat cancer, Nature Review Cancer, 15, 457-472, Publication Date: Aug. 2015 (Year: 2015).*
Linch et al., OX40 agonists and combination immunotherapy: putting the pedal to the metal, Frontiers in Onclology, vol. 5, article 34, Publication Date: Feb. 2015 (Year: 2015).*
Adams et al., Big opportunities for small molecules in immuno-oncology, Nature Reviews, 14, 603-621 (Year: 2015).*
Dunn et al. "Increased T cell cytotoxicity by Betathine-induced upregulation of TNFalpha" International Journal of Immunopharmacology 22(3): 213-227 (2000). abstract.
Taub, F., et al., "Combination Checkpoint Inhibitor Therapy: Anti-PD1 and Beta-alethine Lead to Complete Responses of Melanoma in a Syngeneic Mouse Model," Cancer Research, vol. 77, No. Suppl. 13, Jul. 2017, pp. LB-191.
Knight, G.D. et al., "Seemingly Diverse Activites of Beta-Alethine," Cancer Research, American Associate for Cancer Research, US, vol. 54, Nov. 1994.
Miller, W.H. Jr., et al., "Beta-Alethine Phase I/II Data: Immune Stimulation in Patients with Follicular Lymphoma and Myeloma with Evidence of Tumor Response and no Significant Toxicity," Blood, 43rd Annual Meeting of the American Society of Hematology, Part 1; Orland, Florida, USA, Dec. 7-11, 2001.

(Continued)

*Primary Examiner* — Peter J Reddig
*Assistant Examiner* — Cheng Lu
(74) *Attorney, Agent, or Firm* — Nixon & Vanderhye P.C.

(57) ABSTRACT

The present disclosure provides methods, kits, and compositions comprising β-alethine and one or more immune modulators and methods to determine when they are advantageous. Particular applications include the use of β-alethine and one or more immune modulators in the treatment of cancer.

5 Claims, 13 Drawing Sheets

(56) References Cited

OTHER PUBLICATIONS

Figure 1A:
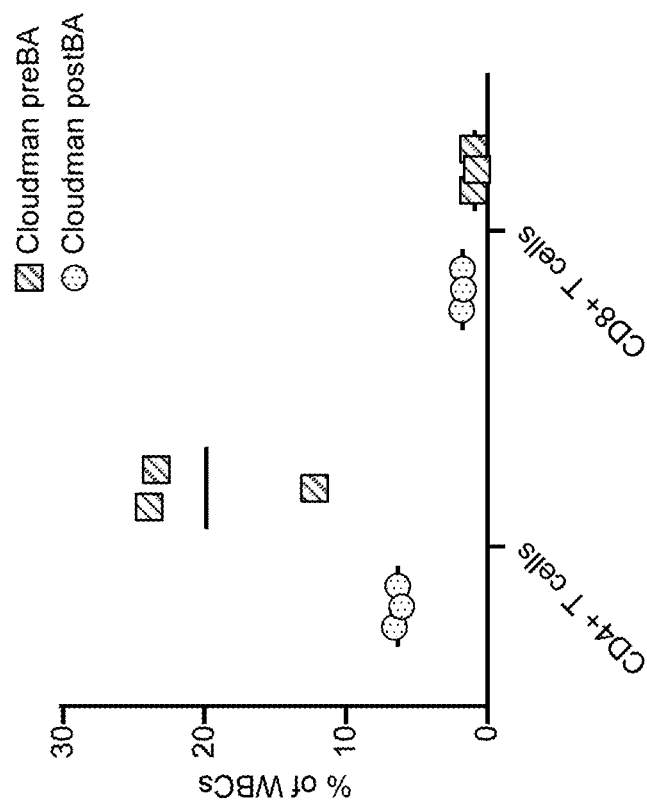

International Search Report for PCT/US2017/06005, dated Mar. 8, 2018.
Written Opinion for PCT/US2017/06005, dated Mar. 8, 2018.
Miller, W. et al., "Beta-Alethine Phase I/II Data: Immune Stimulation in Patients with Follicular Lymphoma and Myeloma with Evidence of Tumor Response and No Significant Toxicity", Presented at the American Society of Hematology, Dec. 8, 2001 by Wilson Miller, M.D. Ph.D. Director of the Clinical Research Program in the Department of Oncology at McGill, University. accessed at https://findcure.org/video/2001presentation.pdf in Nov. 2021, 10 pages.

* cited by examiner

BETA-ALETHINE, IMMUNE MODULATORS, AND USES THEREOF

CROSS REFERENCE TO RELATED APPLICATIONS

This application is a U.S. National Phase of PCT Application No. PCT/US2017/060005, filed Nov. 3, 2017, which claims the priority benefit of U.S. Provisional Application Nos. 62/417,992, filed Nov. 4, 2016; 62/432,663, filed Dec. 11, 2016; 62/439,024, filed Dec. 24, 2016; 62/449,090 filed Jan. 22, 2017; and 62/470,571, filed Mar. 13, 2017; each of which is hereby incorporated by reference herein in its entirety.

BACKGROUND OF THE INVENTION

Field of the Invention

The field of this invention generally relates to the treatment of diseases with (β-alethine and immune modulators.

Background of the Invention

Cancer is one of the leading causes of death in the developed world, with over one million people diagnosed with cancer and 500,000 deaths per year in the United States alone. Overall, it is estimated that 1 in 3 people will develop some form of cancer during their lifetime.

β-alethine (Betathine™, Beta LT™, BLT, BT, β-alanyl-cysteamine disulfide; herein also referred to as BA) is a stable, low molecular weight dimer (MW 367) composed of two small thiols. β-alethine [(H$_2$NCH$_2$CH$_2$(C=O)NHCH$_2$CH$_2$S)$_2$] can be produced by oxidation of the mono-sulfide β-aletheine [H$_2$NCH$_2$CH$_2$(C=O)NHCH$_2$CH$_2$SH] (also β-alanyl-cysteamine), which is unstable in air and aqueous solutions. See U.S. Pat. No. 6,046,241, which is incorporated by reference herein in its entirety. β-alethine is stabilized by its acid salts, especially as a hydrochloride salt having the formula:

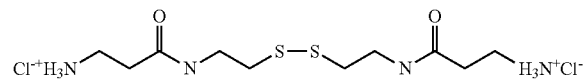

β-alethine has previously been found to be non-toxic in animals, and methods of producing a high-yield, high purity β-alethine product suitable for pharmaceutical use are known in the art. See, for example, U.S. Pat. No. 6,046,241.

β-alethine has diverse biological activity. It is a differentiation compound which has been shown to promote replicative potential (e.g., by delaying senescence of cells in vitro) and diversity of cellular function (e.g., by expanding phenotypic cellular expression) (U.S. Pat. No. 6,245,561, which is incorporated by reference herein in its entirety). It also modulates the expression of various cytokines and can be administered to an animal to bias the immune system toward producing a polarized Th1 response in human peripheral blood mononuclear cells, with increased T cell activation and proliferation, increased IFN-γ production, and depressed IL-10 expression (U.S. Pat. No. 6,451,853, which is incorporated by reference herein in its entirety).

β-alethine has been shown to exhibit potent anti-tumor activity in vivo. In pre-clinical models, β-alethine has been efficacious in treating myeloma, melanoma, and breast cancer. For example, in an NS-1 mouse myeloma model, repeated administration of β-alethine as a monotherapy soon after inoculation with relatively low doses of tumor significantly increased survival rates. Treatment with β-alethine was also found to increase the percent survival in the Cloudman S-91-DB/2 murine model in which melanomas had already been established. See U.S. Pat. Nos. 5,643,966; 6,046,241; and 6,245,561, which are incorporated by reference herein in their entirety. With respect to breast cancer, β-alethine has been shown to be effective in treating localized tumor growth in MT-1 tumor xenograft mice (WO-1999/042099, which is incorporated by reference herein in its entirety).

β-alethine has been used as an adjunct to chemotherapy in treating advanced and aggressive tumors. In two aggressive murine tumor models, β-alethine was administered along with melphalan in the treatment of the MOPC-315 myeloma and with cyclophosphamide in the treatment of the B16 melanoma. In both model systems, combination therapy of β-alethine with chemotherapeutics was more effective than the chemotherapeutic alone, resulting in reduction of both primary tumor size and in the development of metastases (WO-1999/042099). β-alethine has also been shown to increase effectiveness of chemotherapy for late stage breast cancer in MT-1 tumor xenograft mice (WO-1999/042099). Of note, β-alethine did not increase toxicity due to the chemotherapy, and, in fact, it appeared to decrease toxicity. In a human Phase I/II clinical trial, β-alethine as a single agent caused no local or systemic drug related adverse events and led to a reduction or stabilization in tumor sized in all patients with lymphoma who were not anergic to recall antigens pre-trial (Miller, W. H. et al., Beta-Alethine Phase I/II Data: Immune Stimulation in Patients with Follicular Lymphoma and Myeloma with Evidence of Tumor Response and no Significant Toxicity. American Society of Hematology, Dec. 8, 2001 presentation, which is incorporated by reference herein in its entirety). Despite the benefits of β-alethine it has not had sufficiently dramatic effect to move forward to complete clinical trials. Development was halted after Phase I/II in about 2000. No further use has occurred. While some lymphoma patients responded with partial tumor reduction, none had the desired completer response. Thus β-alethine, like checkpoint inhibitors used as monotherapy, are partially effective. Since the molecular mechanism of action of β-alethine has not been elucidated there is no logical manner in which to proceed. No progress has been made for over 15 years.

The immune system has immune checkpoints that serve to avoid the development of auto-immune responses by inhibiting immune cell activation (e.g., immune cell expansion, survival, differentiation, recruitment, and/or activity). This occurs, for example, by the binding of ligands to particular receptors present on the surface of immune cells. While this may prevent autoimmunity, it can also diminish or eliminate the ability of the immune system to fight infections and cancers. Within an environment where the immune system is being limited, including cancer and infectious disease, the presence of a family of negative regulatory molecules, collectively known as "checkpoint inhibitors," can inhibit T cell function to suppress anti-tumor immunity. Checkpoint inhibitors, also referred to as inhibitory immune checkpoint molecules, include, for example, PD1 (also called PDCD1 or CD279); PD-L1 (also called B7-H1 or CD274); PD-L2 (also called B7-DC or CD273); CTLA-4 (also called CD152); B7-H3 (also called CD276); B7-H4 (also called B7S1 or B7x); CD66a (CEACAM1); VISTA (also called B7-H5 or GI24); BTLA; CD160; LAG3 (also called CD223 or Lymphocyte activation gene 3); Indoleamine 2,3-dioxygenase (also called IDO); Galectin-9 (also called LGALS9); TIM-3 (also called HAVCR2); 2B4 (also called CD244); SIRP alpha (also called CD172a); CD39; CD47; CD48 (also called SLAMF2); A2AR; KIRs; and TIGIT (also called VSTM3).

Checkpoint inhibitors attenuate T cell proliferation and cytokine production. Targeted blockage of checkpoint inhibitors using immune modulators promotes the expansion, survival, differentiation, recruitment, function, and/or activity of immune cells and thus act as antagonists of inhibitor checkpoint inhibitors. This targeted blockage can enhance the ability of animals to fight cancer.

Key immune regulators include both those that slow down or inhibit the immune system and those that stimulate the immune system. The former are called "checkpoint molecules" and the drugs that inhibit them are called "immune checkpoint inhibitors" (ICIs). The latter have most often been called co-stimulatory molecules, or sometimes, stimulatory molecules and in some cases "stimulatory immune checkpoint molecules" or "costimulatory immune checkpoint molecules". Stimulatory immune checkpoint molecules include both receptors and ligands. While most immune modulator drugs currently used work antagonistically against checkpoint inhibitors, some, like anti-OX-40, anti-CD137 antibodies, and OX-40 ligand (OX-40L), act as an agonist of a stimulatory or co-stimulatory immune checkpoint molecule. Upon ligand binding and/or activation of the stimulatory immune checkpoint molecule, a cell's anti-tumor immunity against a variety of tumors is enhanced.

These stimulatory immune checkpoint molecules include, but are not limited to, the following receptors and ligands: OX-40 (also called CD134); CD226 (also called DNAM-1); CD137 (also called 4-1BB); CD40L (also called CD154 or TNFSF5); 4-1BBL (also called CD137L); OX-40L (also called TNFSF4 or CD252); CD27; TNFSF14 (also called LIGHT or CD258); CD70 (also called CD27L or TNFSF7); CD80 (also called B7-1); CD86 (also called B7-2); GITR (CD357); GITR Ligand (also called TNFSF18); ICOS (CD278); ICOS Ligand (also called B7-H2); HVEM (also called TNFRSF14); DR3; CD28; CD30; CD30L (TNFSF8); TL1A; Nectin-2 (CD112); CD40; CD96; IL-2R (CD122); and CD155 (also called PVR).

Both these groups of immune modulators, those that act to inhibit inhibitory checkpoints and those that act to stimulate/activate stimulatory immune checkpoint molecules (sometime also called "stimulatory checkpoints") have been shown to enhance the immune system and be effective therapies for cancers and infections. Anti-PD-1, anti-PDL1 and anti-CTLA-4 antibodies have been approved for cancer therapy and represent significant advances in treatment. In late stage patients, response rates have ranged between 10% (even less for some cancers) and 61%; thus the vast majority of patients need additional therapy. Kavecansky and Pavlick; *AJHO.* 13(2):9-20 (2017). In addition, different tumors, even with the same underlying histology, show a wide range of heterogeneity in how they suppress the immune system, with tumors variably expressing PD-1 or having different quantities of infiltrating lymphocytes. Scognamiglio et al., *Int J Mol Sci.* 17(5) (2016), which is incorporated by reference herein in its entirety.

Similarly, infectious diseases, such as tuberculosis (TB), may be associated with high levels of inhibitory molecules such as PDL1 and ligand for TIM3. See Dyck, L. et al., *Eur J Immunol.* 47(5):765-79 (2017); Hassan, S. S., et al., *PLoS One* 10(9):e0137646 (2015); and Jayaraman, P. et al. *PLoS Pathog.* 12(3):e1005490 (2016), which are incorporated by reference herein in their entirety. These inhibitory immune checkpoint molecules inhibit the immune response and allow disease to continue and expand. Thus it is very important to mobilize the immune system as antibiotics may have limited benefit and the immune system is needed to clear infections. The latter is illustrated by late stage HIV patients who cannot be keep alive, despite antibiotics, if their immune system has been destroyed.

Thus, there remains an unmet medical need for more effective therapies for the treatment of cancers and infectious diseases in situations where there is inhibitory immune system functioning or a lack of stimulatory function. Disclosed herein are compositions, kits, and methods relating to therapies using β-alethine, including, but not limited to, combination therapies using β-alethine and immune modulators for the treatment of cancer.

SUMMARY OF THE INVENTION

The present disclosure provides pharmaceutical compositions comprising (β-lalethine and an immune modulator, wherein the immune modulator is an antagonist of an inhibitory immune checkpoint molecule or an agonist of a stimulatory immune checkpoint molecule. In one aspect, the immune modulator promotes the expansion, survival, differentiation, recruitment, function, and/or activity of immune cells. In another embodiment, the disclosure provides pharmaceutical kits comprising at least two compartments, one compartment comprising β-alethine and another compartment comprising an immune modulator.

In another embodiment, the disclosure provides methods of treating or preventing a disease in a subject in need thereof, which comprises administering to the subject an effective amount of a combination of β-alethine and an immune modulator, wherein the administration of β-alethine occurs before, concurrently with, or after the administration of the immune modulator, and wherein the immune modulator is an antagonist of an inhibitory immune checkpoint molecule or an agonist of a stimulatory immune checkpoint molecule. In one aspect, the immune modulator promotes the expansion, survival, differentiation, recruitment, function, or activity of immune cells. In another embodiment, the disclosure provides methods of potentiating the effect of an immune modulator during the treatment in a subject.

In another embodiment, the disclosure provides methods of treating or preventing cancer in a subject in need thereof, which comprises administering to the subject an effective amount of a combination of β-alethine and an immune modulator, wherein the administration of β-alethine occurs before, concurrently with, or after the administration of the immune modulator, and wherein the immune modulator is an antagonist of an inhibitory immune checkpoint molecule or an agonist of a stimulatory immune checkpoint molecule. In one aspect, the immune modulator promotes the expansion, survival, differentiation, recruitment, function, or activity of immune cells. In another embodiment, the disclosure provides methods of potentiating the effect of an immune modulator during the treatment of cancer in a subject.

In one embodiment, the methods of the disclosure comprise detecting and measuring the expression level of an inhibitory immune checkpoint molecule or stimulatory immune checkpoint molecule in an immune cell or cancer cell sample from the subject. In another embodiment, disclosed herein are methods of determining the efficacy of β-alethine therapy for the treatment of cancer in a subject in need thereof, the methods comprising determining whether ex vivo treatment of an immune cell or cancer cell sample from the subject with β-alethine reduces the expression level of an inhibitory checkpoint molecule. In another embodiment, disclosed herein are methods of determining the efficacy of β-alethine therapy for the treatment of cancer in a subject in need thereof, the methods comprising determining whether ex vivo treatment of an immune cell or cancer cell sample from the subject with β-alethine increases the expression level of a stimulatory checkpoint molecule.

In another embodiment, the methods of treating or preventing cancer disclosed herein comprise identifying a subject with an immune cell or cancer cell sample that has an expression level of an inhibitory immune checkpoint molecule higher than a predetermined value, and administering to said subject an effective amount of β-alethine.

In another embodiment, the methods of treating or preventing cancer disclosed herein comprise identifying a subject with an immune cell or cancer cell sample that has an expression level of a stimulatory immune checkpoint molecule lower than a predetermined value, and administering to said subject an effective amount of β-alethine.

In yet another embodiment, disclosed herein are methods of inhibiting tumor growth in a subject having cancer, the method comprising injecting an effective amount of β-alethine into the tumor of the subject.

In another embodiment, the disclosure provides methods of treating or preventing an infectious disease in a subject in need thereof, which comprises identifying a subject with an immune cell sample that has an expression level of an inhibitory immune checkpoint molecule higher than a predetermined value, and administering to the subject an effective amount of β-alethine.

In another embodiment, the disclosure provides methods of treating or preventing an infectious disease in a subject in need thereof, which comprises identifying a subject with an immune cell sample that has an expression level of a stimulatory immune checkpoint molecule lower than a predetermined value, and administering to the subject an effective amount of β-alethine.

In another embodiment, the disclosure provides a method of treating or preventing an infectious disease in a subject in need thereof, which comprises detecting the expression level of an inhibitory immune checkpoint molecule in an immune cell sample from the subject, and, if the expression level is higher than a predetermined value, administering an effective amount of β-alethine.

In another embodiment, the disclosure provides a method of treating or preventing an infectious disease in a subject in need thereof, which comprises detecting the expression level of a stimulatory immune checkpoint molecule in an immune cell sample from the subject, and, if the expression level is lower than a predetermined value, administering an effective amount of β-alethine.

In another embodiment, the disclosure provides a method of treating or preventing an infectious disease in a subject in need thereof, which comprises determining whether ex vivo treatment of an immune cell sample from the subject with β-alethine reduces the expression of an inhibitory checkpoint molecule; and if so, administering an effective amount of β-alethine to the subject.

In another embodiment, the disclosure provides a method of treating or preventing an infectious disease in a subject in need thereof, which comprises determining whether ex vivo treatment of an immune cell sample from the subject with β-alethine increases the expression of a stimulatory checkpoint molecule; and if so, administering an effective amount of β-alethine to the subject.

In another embodiment, the disclosure provides a method of determining the efficacy of β-alethine therapy for the treatment or prevention of an infectious disease in a subject in need thereof, which comprises detecting the expression level of an inhibitory checkpoint molecule in an immune cell sample from the subject, wherein an expression level higher than a predetermined value indicates that the subject is likely to respond favorably to β-alethine therapy.

In another embodiment, the disclosure provides a method of determining the efficacy of β-alethine therapy for the treatment or prevention of an infectious disease in a subject in need thereof, which comprises detecting the expression level of a stimulatory checkpoint molecule in an immune cell sample from the subject, wherein an expression level lower than a predetermined value indicates that the subject is likely to respond favorably to β-alethine therapy.

Further objects and advantages of the present invention will be clear from the description that follows.

BRIEF DESCRIPTION OF THE DRAWINGS/FIGURES

Figure 1B:
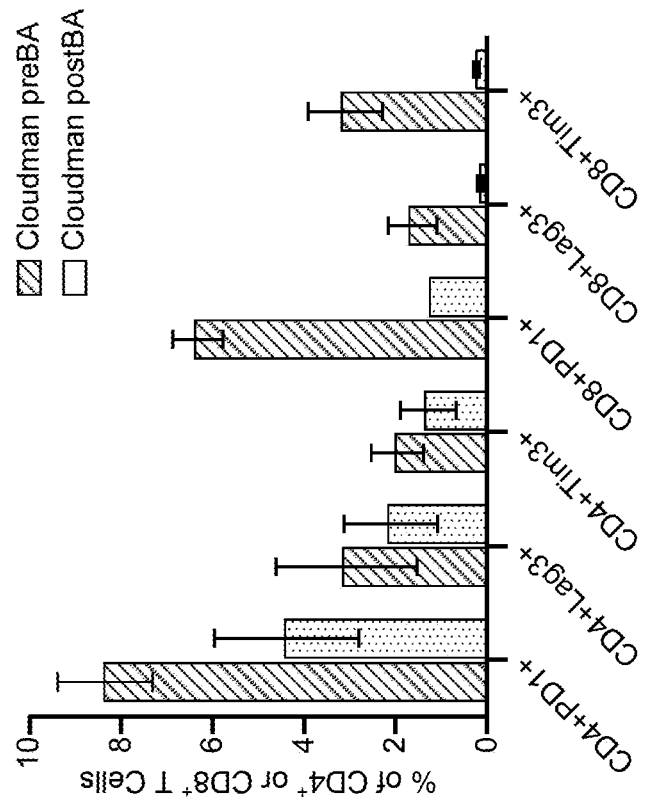
Figure 1C:
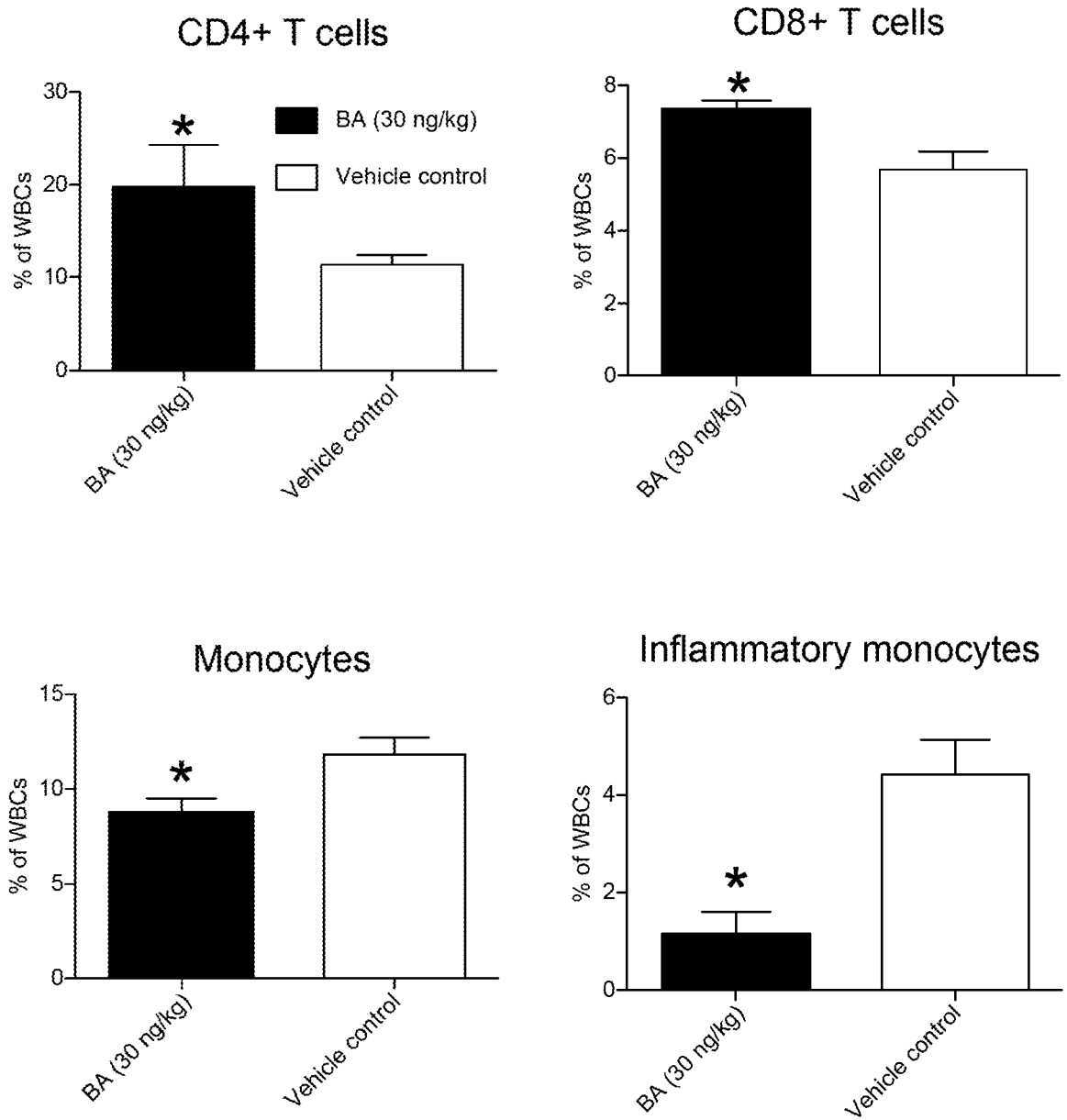

FIG. 1A shows the percentage of CD4+ or CD8+ T cells that are positive for checkpoint inhibitors (PD-1, Lag3, and Tim3) before and after a subcutaneous (s.c.) single injection of β-alethine in mouse melanoma model. FIG. 1B shows the percentage of white blood cells (WBCs) that are CD4+ positive T cells before and after a single s.c. injection of β-alethine in mouse melanoma model. Cloudman preBLT: blood taken prior to β-alethine treatment; Cloudman postBLT: blood taken 48 hours after β-alethine treatment. n=3 mice. FIG. 1C shows the percentage of white blood cells (WBCs) that are CD4+ positive T cells, CD8+ T cells, monocytes, and inflammatory monocytes in blood of mice 7 days after s.c. treatment with β-alethine (BA) or a vehicle control. (*=p<0.05). n=3 mice.

Figure 2:
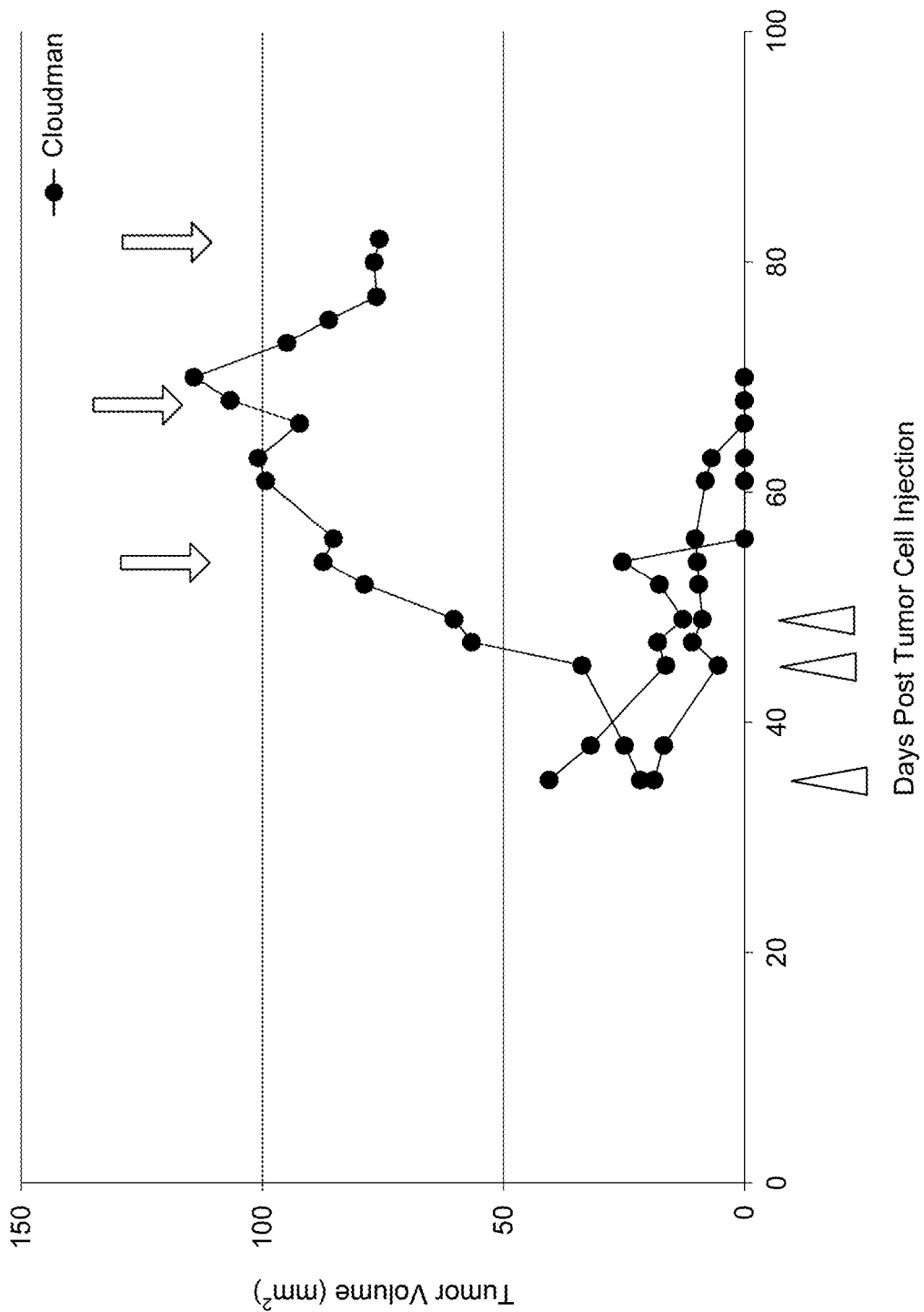

FIG. 2 shows tumor size (in $mm^2$) of three animals with established melanoma tumors. Tumor size was measured beginning 38 days after injection of 100,000 cells from a Cloudman melanoma cancer cell line. Triangles: subcutaneous (s.c.) injections of β-alethine were administered at days 38, 46, and 52 to all three mice; arrows: intra-tumoral injections of β-alethine were administered at days 55, 68, and 82 into one of the three mice, whose tumor continued to grow even after the s.c. β-alethine injections.

Figure 3A:
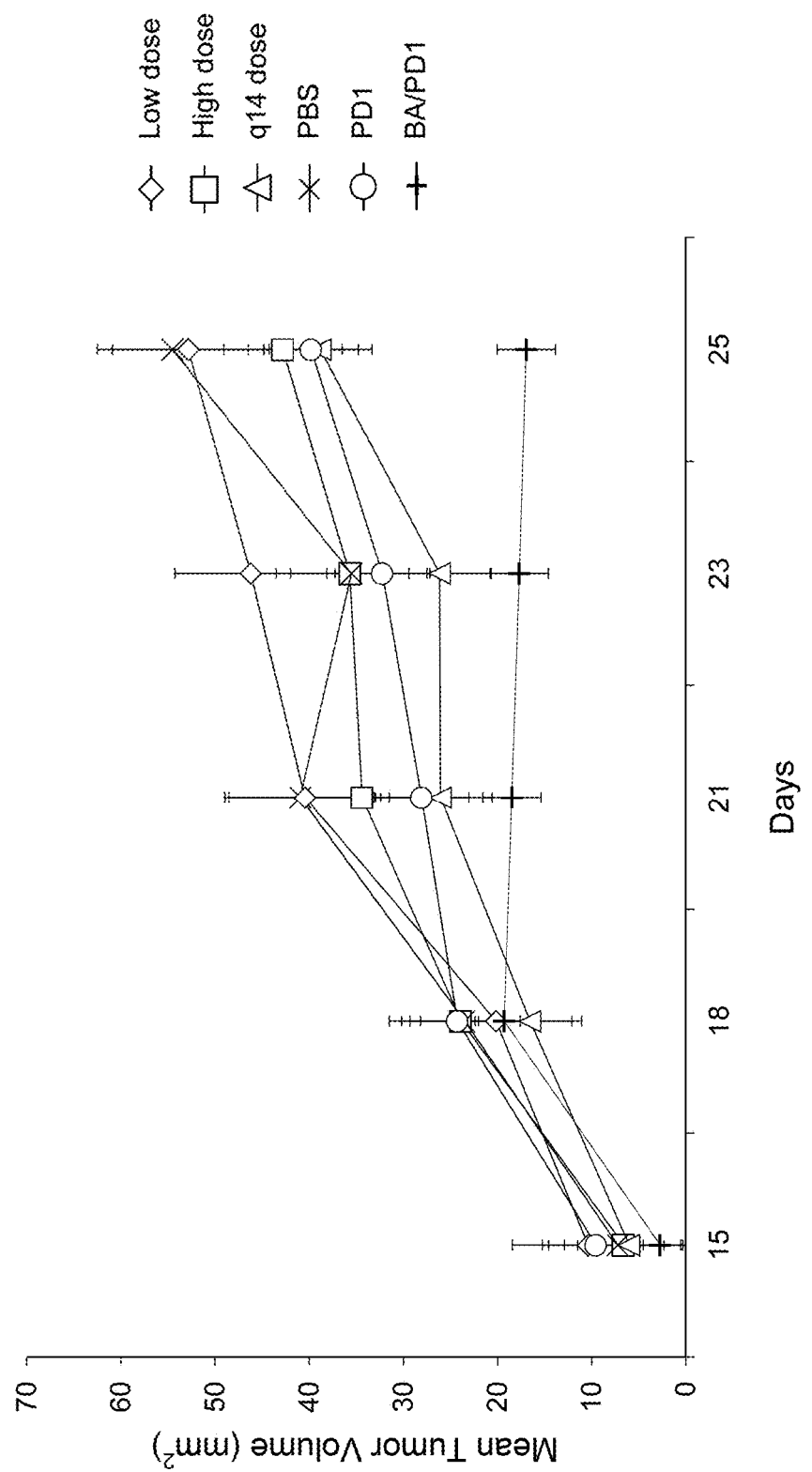
Figure 3B:
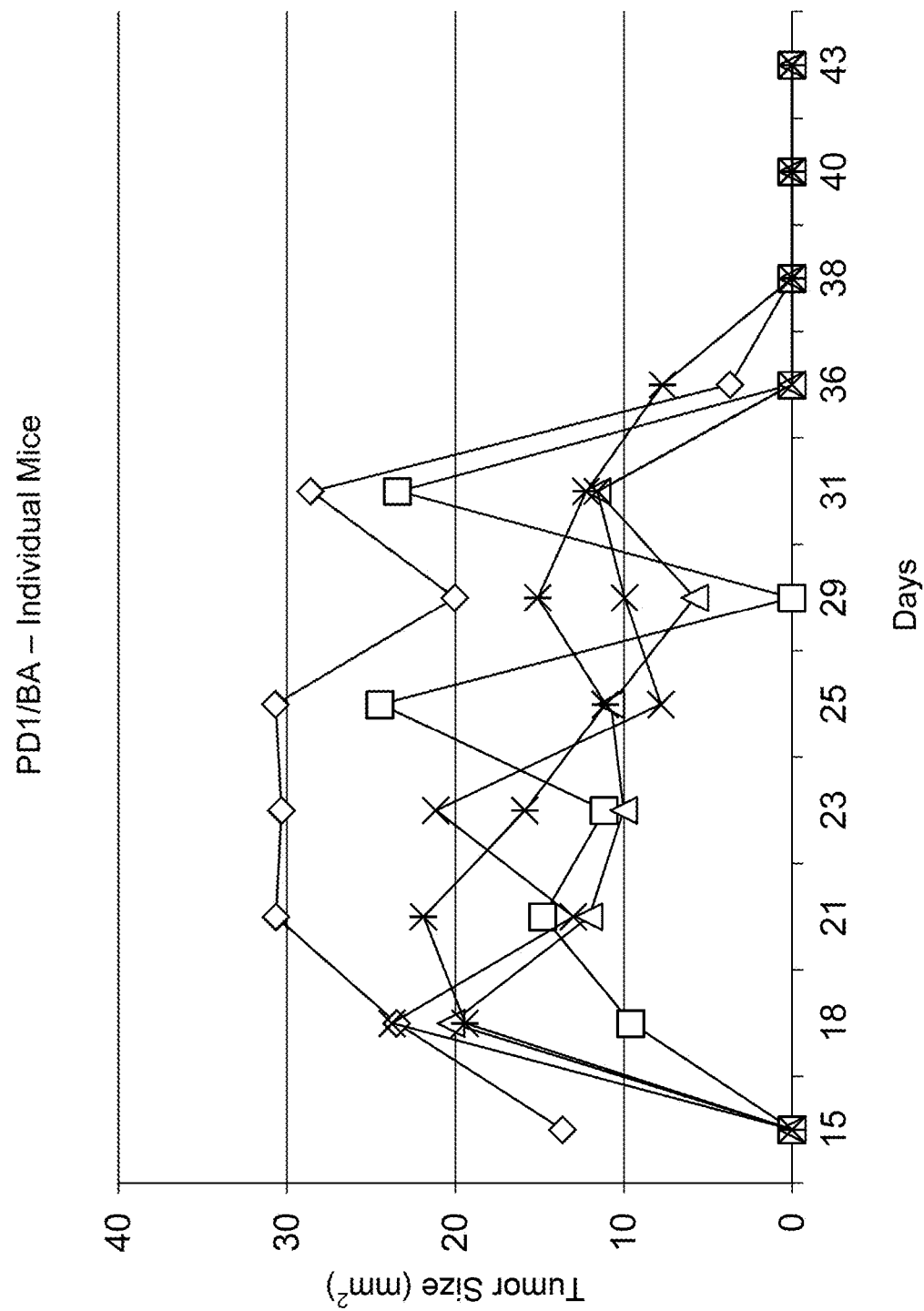
Figure 3C:
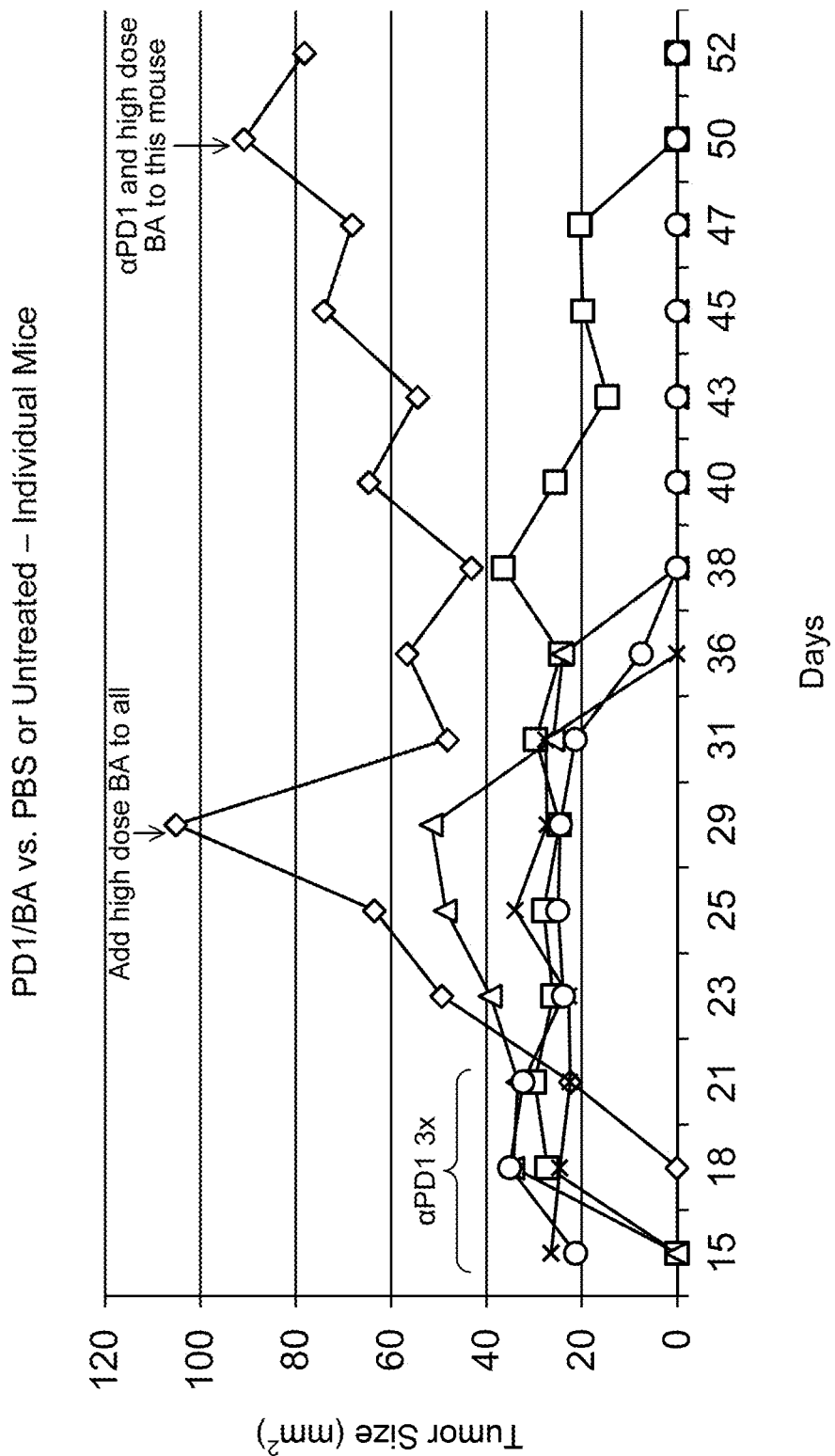

FIG. 3A shows tumor size (in $mm^2$) of mice treated with various doses of (β-alethine with or without a checkpoint inhibitor, PD-1. Tumor size was measured beginning 15 days after injection of 150,000 cells from a Cloudman melanoma cancer cell line. Low dose: s.c. injection of 30 ng/kg β-alethine once a week starting on day 15; High dose: s.c. injection of 30 mg/kg β-alethine once a week starting on day 15; q14 dose: s.c. injection of 30 ng/kg β-alethine every 14 days starting on day 15; PBS: 100 µl s.c. injection every week starting on day 15; PD-1: intraperitoneal (i.p.) injection of an anti-PD-1 antibody at 50 µg/mouse; BLT/PD-1: s.c. injection of 30 mg/kg β-alethine once a week and i.p. injection of an anti-PD-1 antibody at 50 µg/mouse every 7 days. n=10 mice per group in Low dose, High dose, q14, and PBS groups. n=5 mice in PD-1 and BLT/PD-1 groups. FIG. 3B shows tumor growth in individual mice from the BLT/PD-1 cohort of FIG. 3A. Each line represents one mouse. FIG. 3C shows tumor growth in individual mice from the originally PD-1 only cohort of FIG. 3A. Each line represents one mouse; at day 29, all five animals were treated with a high dose (30 mg/kg) of β-alethine. Tumor size was measured in $mm^2$.

Figure 4:
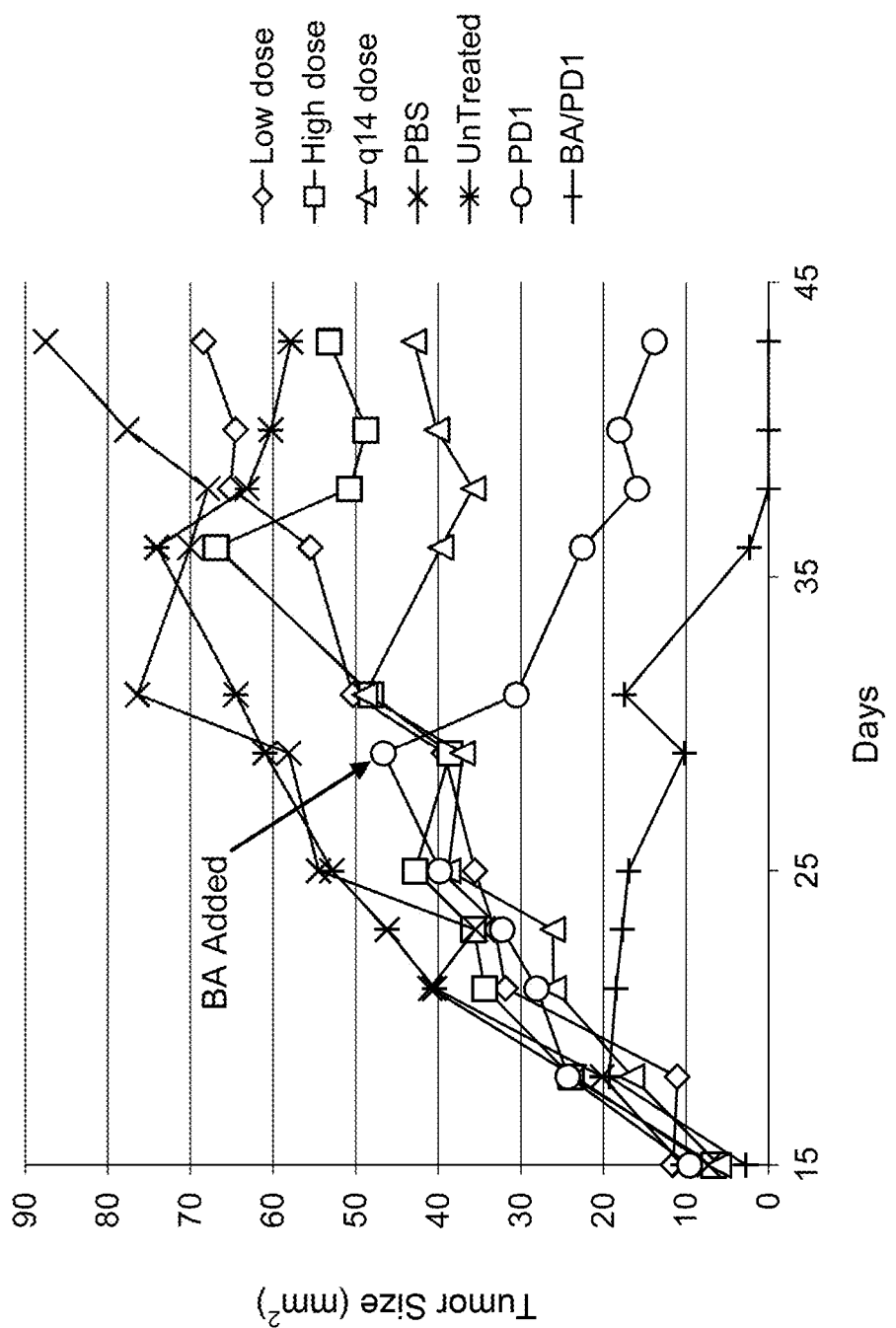

FIG. 4 shows tumor size of mice treated with various doses of β-alethine with or without a checkpoint inhibitor, PD-1. Tumor size was measured beginning 15 days after injection of 150,000 cells from a Cloudman melanoma cancer cell line. Low dose: s.c. injection of 30 ng/kg β-alethine once a week starting on day 15; High dose: s.c. injection of 30 mg/kg β-alethine once a week starting on day 15; q14 dose: s.c. injection of 30 ng/kg β-alethine every 14 days starting on day 15; PBS: 100 µl s.c. injection every week starting on day 15; Untreated: no injection; PD-1: i.p. injection of an anti-PD-1 antibody at 50 µg/mouse at days 15, 18, and 21 and s.c. injection of 30 mg/kg β-alethine once a week starting on day 29; BLT/PD-1: s.c. injection of 30 mg/kg β-alethine once a week starting on day 15 and i.p. injection of an anti-PD-1 antibody at 50 µg/mouse every 7 days starting on day 15. n=10 mice per group in Low dose, High dose, q14, PBS, and untreated groups. n=5 mice in PD-1 and BLT/PD-1 groups.

Figure 5:
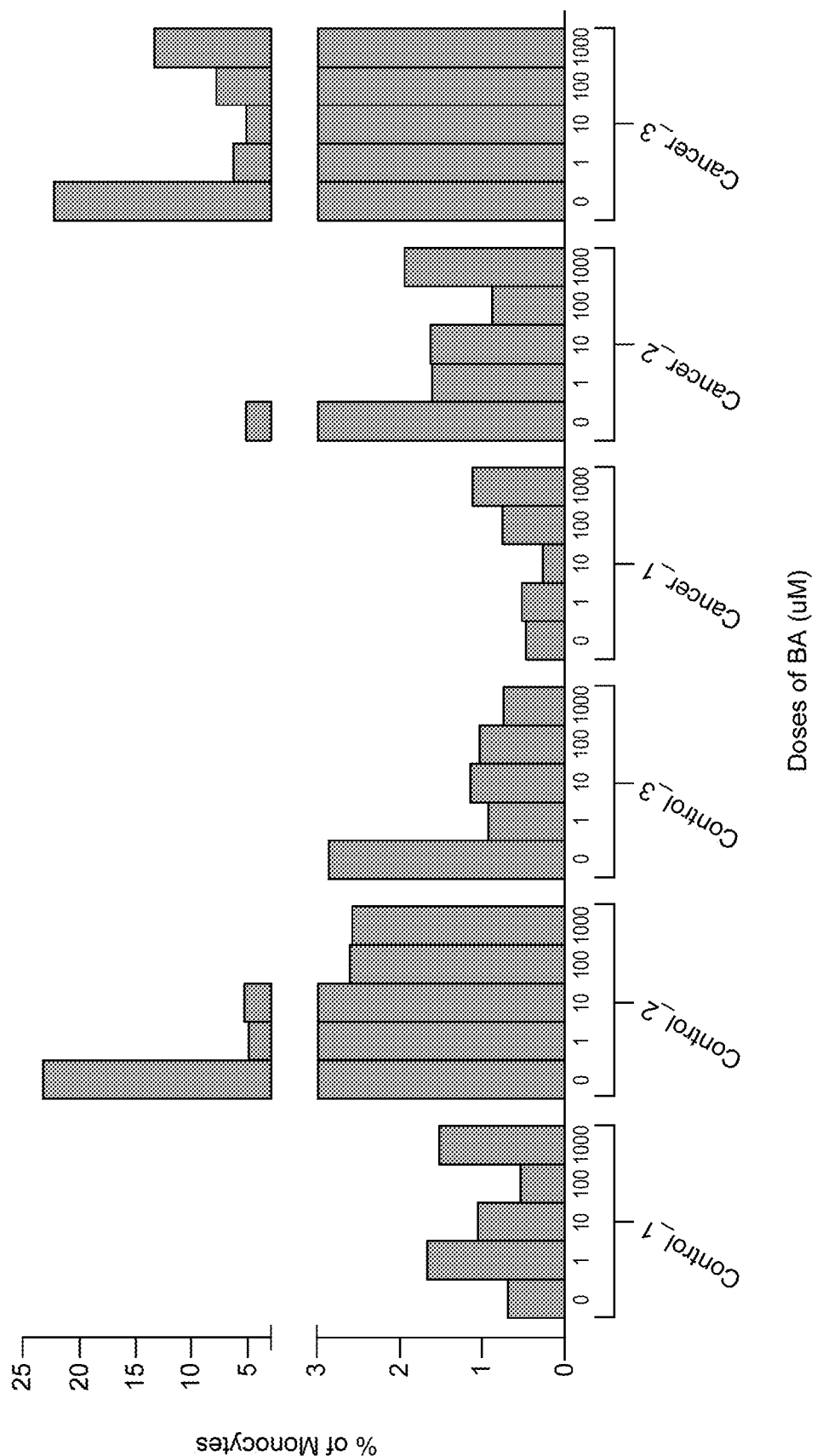

FIG. 5 shows percentage of monocytes positive for PD-L1 in isolated white blood cells from dogs 24 hours after ex vivo treatment with 0 uM (negative control); 1 uM, 10 uM, 100 uM, and 1000 uM β-alethine. In total, three healthy dogs and three dogs with cancer were treated with β-alethine. Cancer_1 and Cancer_2: osteosarcoma; Cancer_3: melanoma.

Figure 6A:
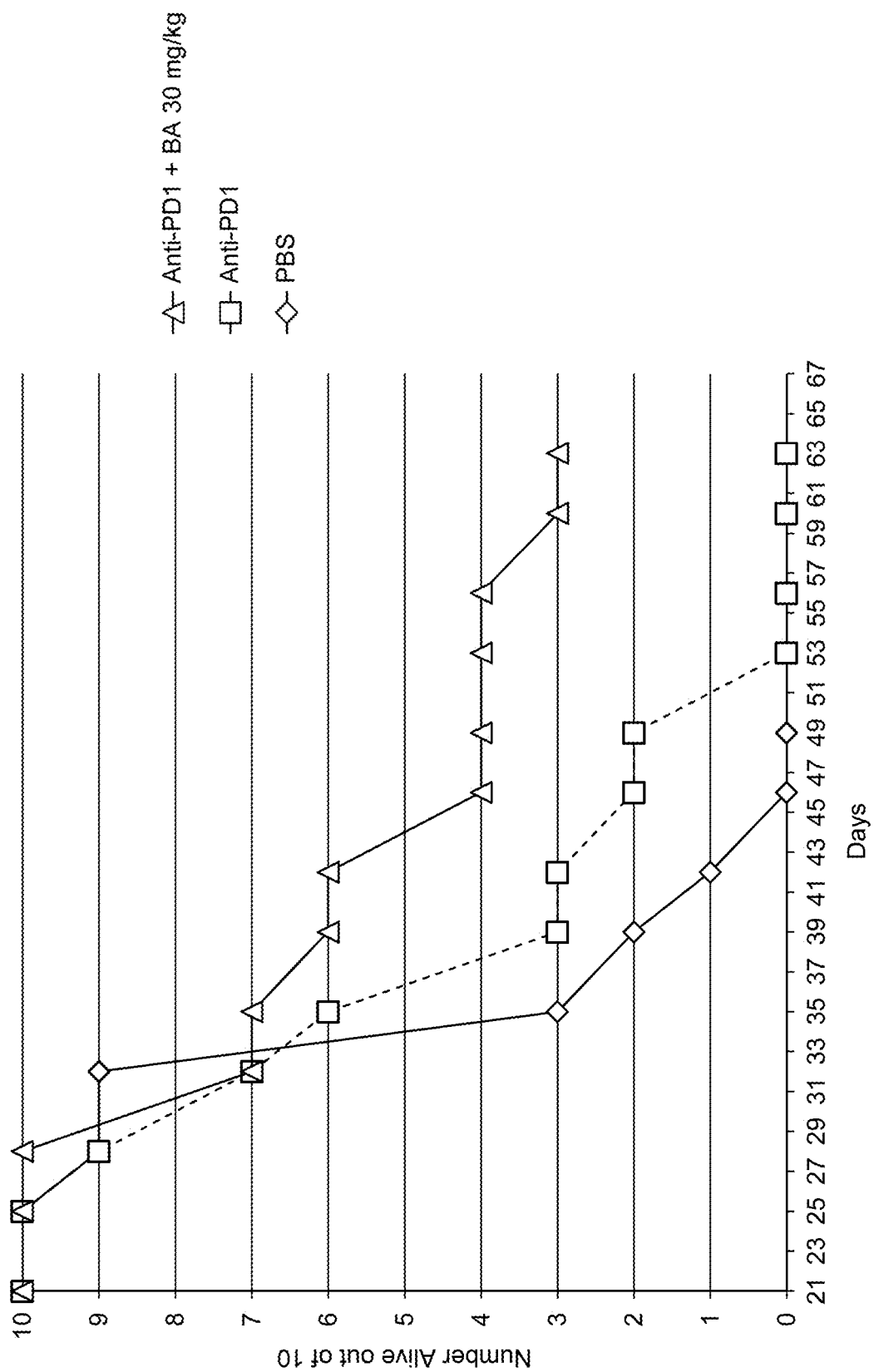
Figure 6B:
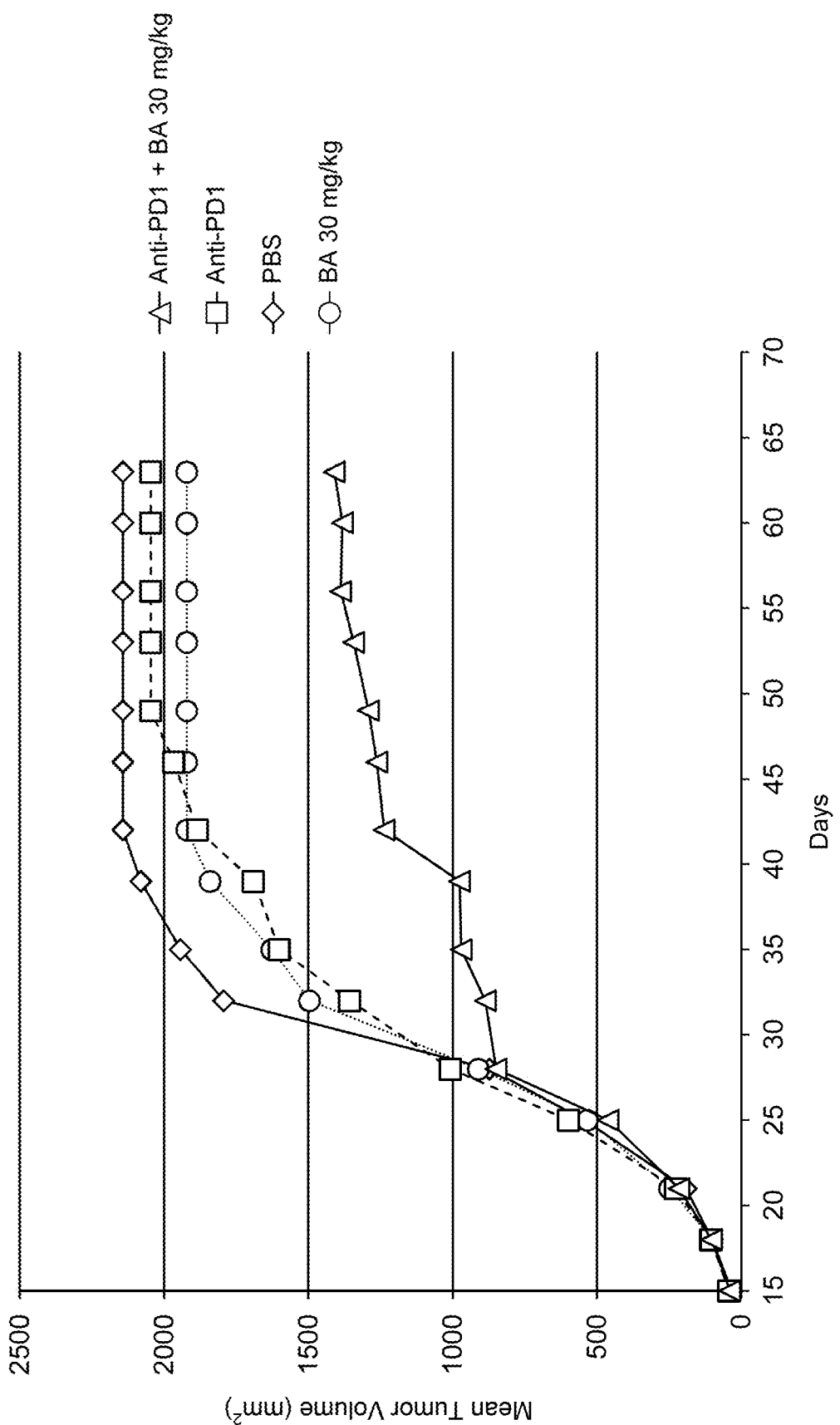
Figure 6C:
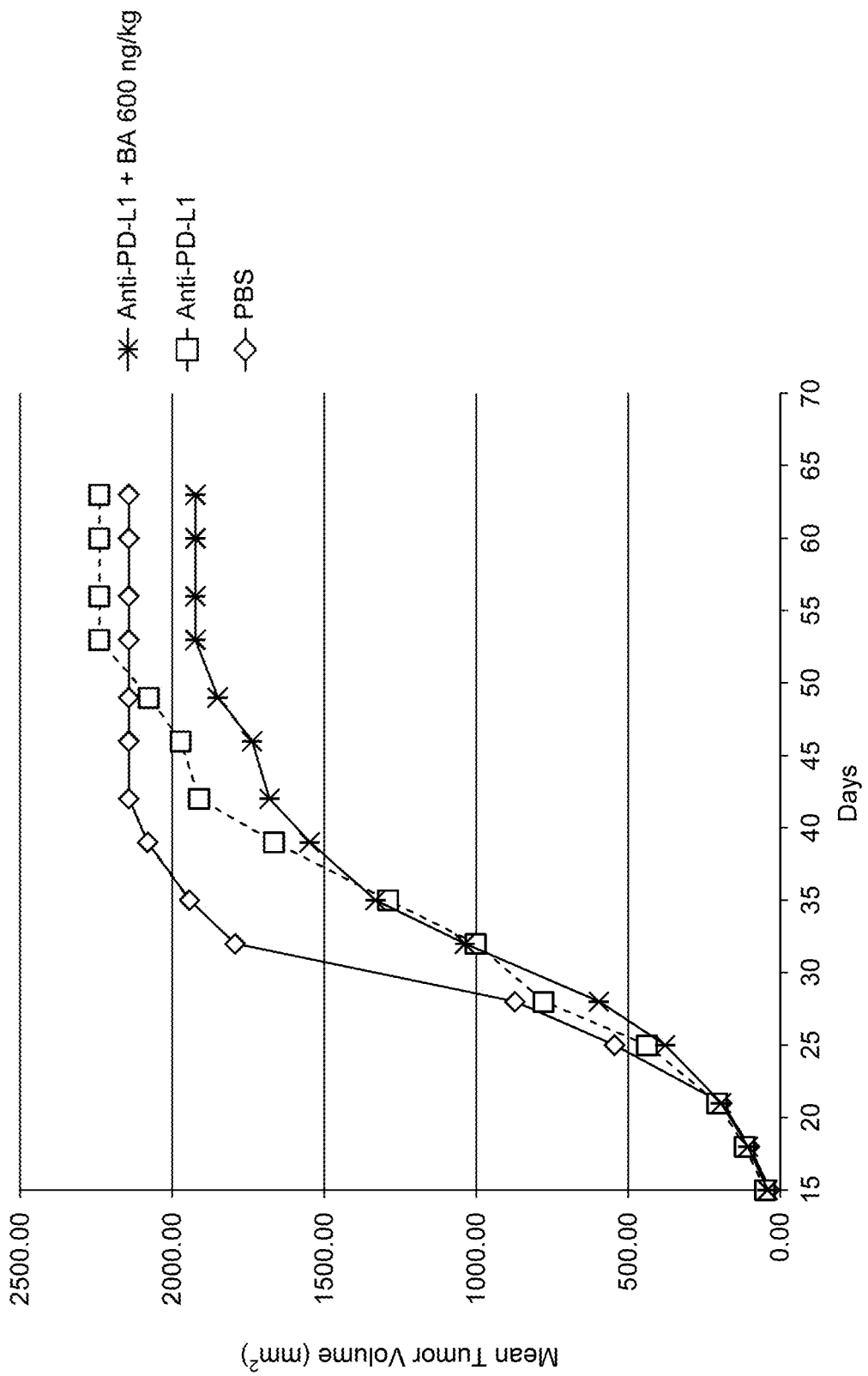
Figure 6D:
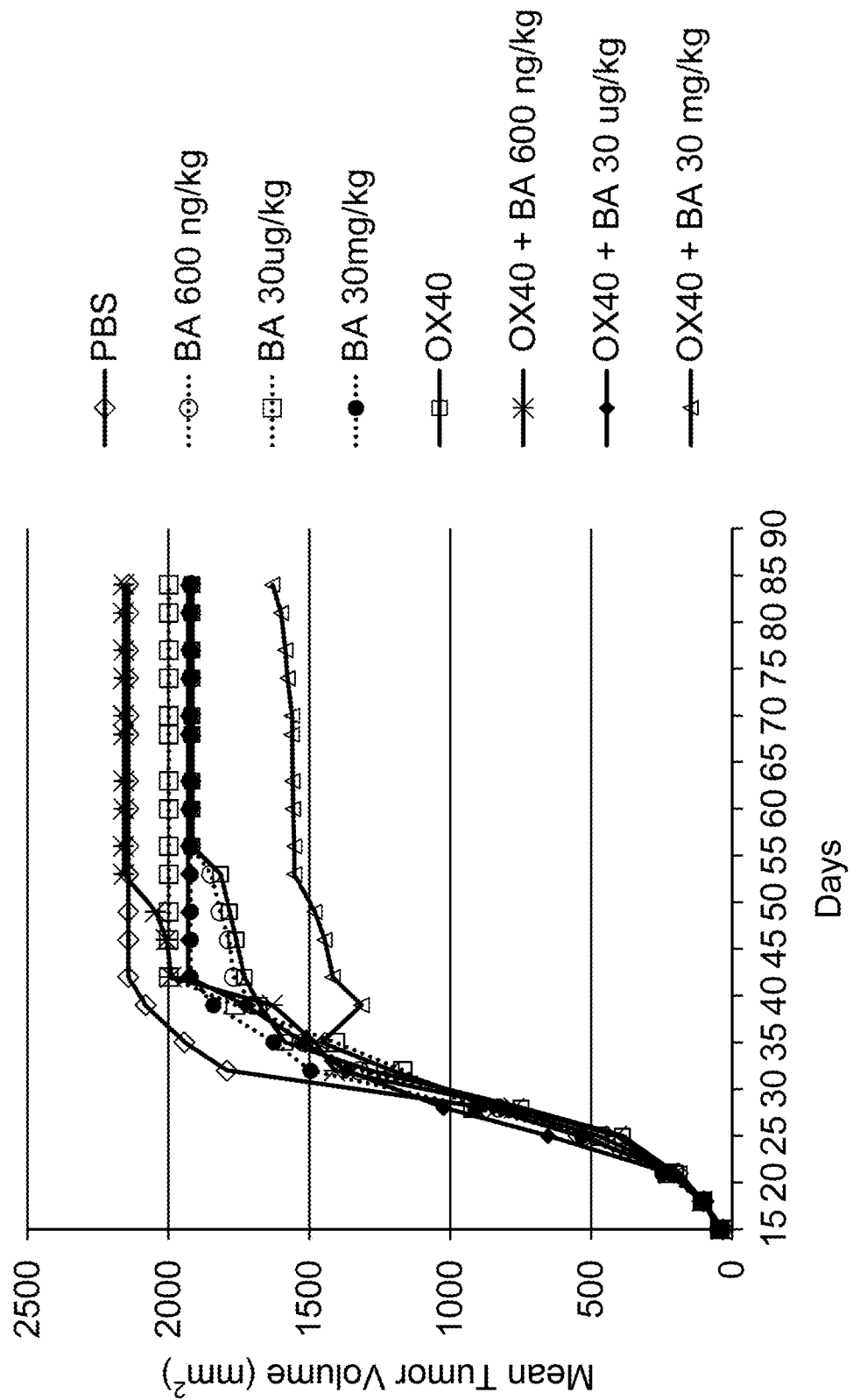
Figure 6E:
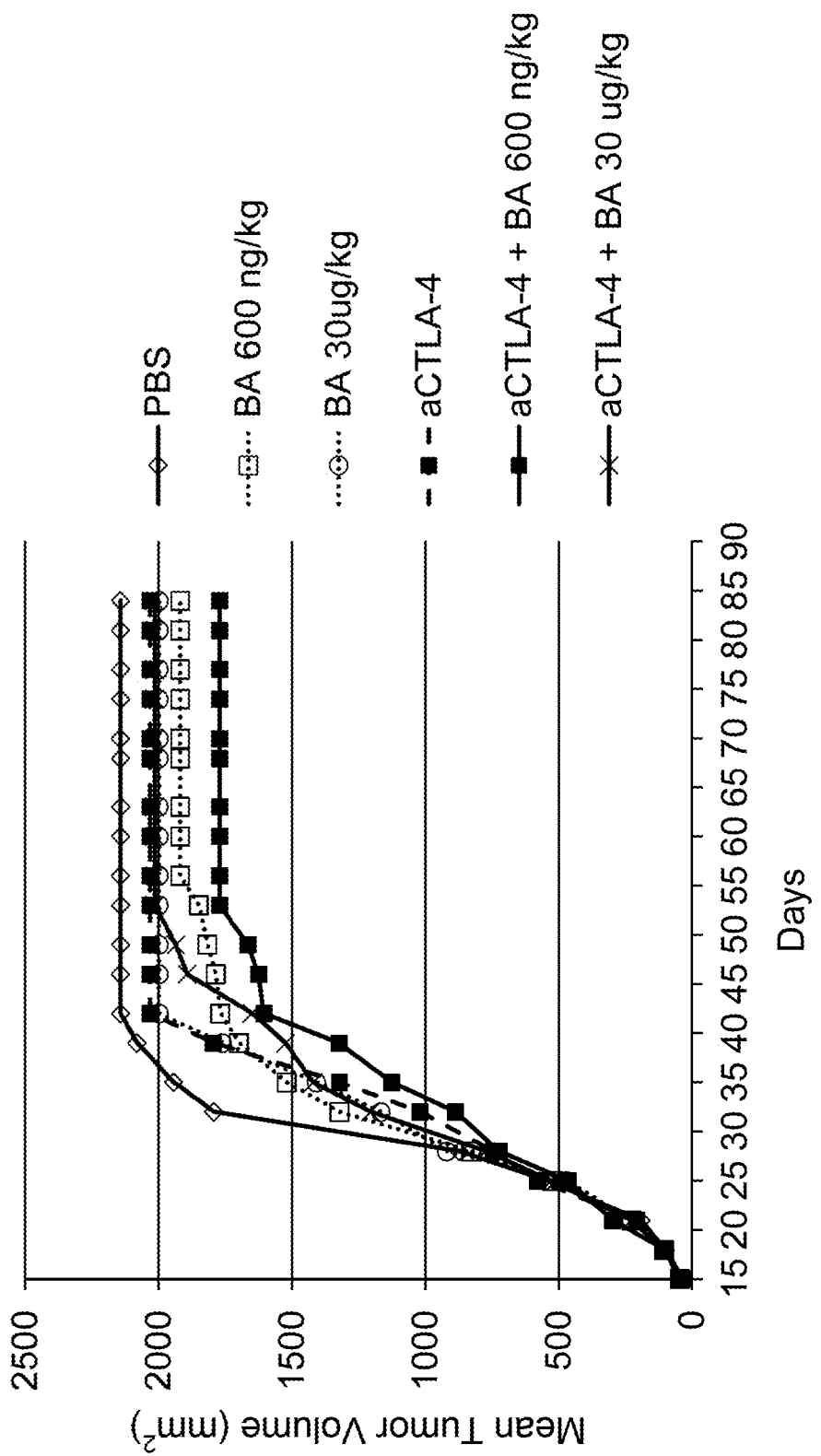

FIG. 6A show survival data in MBT-2 mouse bladder cancer model. Anti-PD-1+β-alethine: triangles; 30 mg/kg β-alethine given s.c. injection at day 17 and thereafter once a week for a total of 4 injections plus 10 mg/kg/inj of anti-PD-1 antibody at day 17 twice a week for a total of 4 injections. Anti-PD-1: squares; 10 mg/kg/inj of anti-PD-1 antibody at day 17 and thereafter twice a week for a total of 4 injections (TW×2 wk). PBS: 100 µl s.c. injections every week for a total of 4 injections starting on day 17. p<0.005. n=10 mice per treatment group. FIG. 6B shows mean tumor volume in mm$^3$ in mouse bladder cancer model from FIG. 6A. N=10 mice per group. FIG. 6C shows mean tumor volume in mm$^3$ in mouse bladder cancer model after combination treatment comprising anti-PD-L1. PBS: 100 µl s.c. injection every week starting on day 17. Anti-PD-L1: 10 mg/kg/inj TW×2 wk. Anti-PD-L1+β-alethine: 10 mg/kg/inj of anti-PD-L1 TW×2 wk and 600 ng/kg of β-alethine once a week for a total of 4 injections beginning on day 17. n=10 mice per group. FIG. 6D shows mean tumor volume in mm$^3$ in mouse bladder cancer model after treatment with PBS; β-alethine alone, or combination treatment of β-alethine and anti-OX-40 antibody. BA: β-alethine. n=10 mice per group. FIG. 6E shows mean tumor volume in mm$^3$ in mouse bladder cancer model after treatment with PBS; β-alethine alone, or combination treatment of β-alethine and anti-CTLA-4 antibody. n=10 mice per group.

DETAILED DESCRIPTION OF THE INVENTION

In the following detailed description, reference is made to the accompanying drawings which form a part hereof, and in which are shown by way of illustration embodiments that may be practiced. It is to be understood that other embodiments may be utilized and structural or logical changes may be made without departing from the scope of the disclosure. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

I. Definitions

Unless otherwise noted, technical terms are used according to conventional usage.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/ database sequence were specifically and individually indicated to be so incorporated by reference.

Although methods and materials similar or equivalent to those described herein may be used in the practice or testing of this disclosure, suitable methods and materials are described below. In addition, the materials, methods, and examples are illustrative only and not intended to be limiting. In order to facilitate review of the various embodiments of the disclosure, the following explanations of specific terms are provided:

As used herein, the terms "about" and "approximately," when used to modify a numeric value or numeric range, indicate that deviations of 5% to 10% above and 5% to 10% below the value or range remain within the intended meaning of the recited value or range.

"Administering" (or any form of administration such as "administered") means delivery of an effective amount of composition to a subject as described herein. Exemplary routes of administration include, but are not limited to, injection (such as subcutaneous, intramuscular, intradermal, intraperitoneal, intratumoral, and intravenous), oral, sublingual, rectal, transdermal, intranasal, vaginal, and inhalation routes.

Administration "in combination with" one or more further therapeutic agents includes simultaneous (concurrent) or consecutive administration in any order and can be either by same route or different routes. If by the same route they may or may not be mixed together first.

"Agonist" refers to or describes an agent that is capable of, directly or indirectly, substantially inducing, activating, promoting, increasing, or enhancing the biological activity of a target and/or a pathway. The term "agonist" is used herein to include any agent that partially or fully induces, activates, promotes, increases, or enhances the function or activity of a protein and/or signaling pathway. An agonist may include a ligand (e.g., OX-40L) of a stimulatory or co-stimulatory immune receptor (e.g., a stimulatory immune checkpoint molecule). An agonist may also include an antibody or antigen binding fragment that binds to and activates a stimulatory or costimulatory immune receptor (e.g., OX-40).

"Antagonist" as used herein refers to any molecule that partially or fully blocks, inhibits, reduces, or neutralizes a biological activity of a target and/or signaling pathway.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, multispecific antibodies such as bispecific antibodies generated from at least two intact antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as radioisotopes, labels, etc.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies.

An "antagonist antibody" or "blocking antibody" is one which inhibits or reduces biological activity of the antigen, receptor, or ligand it binds, such as PD- or PD-L1. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

"β-alethine" (or beta alethine) refers to the compound 3-amino-N-(2-{[2-(3-aminopropanamido) ethyl]disulfanyl}ethyl)propenamide, or beta-alanyl cysteamine disulfide and its derivatives.

A "cancer cell sample," as used herein, refers to a cell sample obtained from a cancer, a cancer region, a tumor, lymph, blood, bone marrow, or a pre-cancerous lesion, including both non-tumorigenic cells, which comprise the bulk of the cancer cell population, and tumorigenic stem cells (cancer stem cells). These cells may also be "circulating cancer cells" or "CTCs" isolated from the blood or cancer cells from ascites, urine, cerebral spinal fluid or other body fluid or cavity. In the case of hematologic cancer (e.g., leukemia, lymphoma, and multiple myeloma), the cancer cell sample may be obtained from the blood or blood-forming tissue, such as the bone marrow.

CD4+ T cells are T cells with CD4 receptors that recognize antigens on the cell surface and secrete lymphokines that stimulate B cells and killer T cells. CD4+ T cells are commonly divided into regulatory T (Treg) cells and conventional T helper (Th) cells.

CD8+ T cells: A CD8+ T cell is a T lymphocyte (a type of white blood cell) that has a CD8 surface molecule. Such cells may kill cancer cells, cells that are infected (particularly with viruses), or cells that are damaged in other ways. Most cytotoxic T cells express T-cell receptors (TCRs) that can recognize a specific antigen. An antigen is a molecule capable of stimulating an immune response, and is often produced by cancer cells or viruses. Antigens inside a cell are bound to class I MHC molecules, and brought to the surface of the cell by the class I MHC molecule, where they can be recognized by the T cell. If the TCR is specific for that antigen, it binds to the complex of the class I MHC molecule and the antigen, and the T cell destroys the cell. In order for the TCR to bind to the class I MHC molecule, the former must be accompanied by a glycoprotein called CD8, which binds to the constant portion of the class I MHC molecule.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The terms "comprising," "including," "having," and the like, as used with respect to embodiments, are synonymous.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A "co-stimulatory immune checkpoint molecule" or "stimulatory immune checkpoint molecule" as used herein, includes both receptors and ligands that enhance the immune system. Stimulatory immune checkpoint molecules are molecules that actively promote immune cell function (e.g., the expansion and proliferation of killer CD8+ and helper CD4+ T cells) to promote anti-tumor immunity. Stimulatory immune checkpoint molecules include both receptors and ligands. While most immune modulator drugs currently used work antagonistically against checkpoint inhibitors, some, like anti-OX-40, anti-CD137 antibodies, and OX-40 ligand (OX-40L), act as an agonist of a stimulatory or co-stimulatory immune checkpoint molecule. Upon ligand binding and/or activation of the stimulatory immune checkpoint molecule, a cell's anti-tumor immunity against a variety of tumors is enhanced. Stimulatory immune checkpoint molecules are disclosed herein and include, but are not limited to the following receptors and ligands: OX-40 (also called CD134); CD226 (also called DNAM-1); CD137 (also called 4-1BB); CD40L (also called CD154 or TNFSF5); 4-1BBL (also called CD137L); OX-40L (also called TNFSF4 or CD252); CD27; TNFSF14 (also called LIGHT or CD258); CD70 (also called CD27L or TNFSF7); CD80 (also called B7-1); CD86 (also called B7-2); GITR (CD357); GITR Ligand (also called TNFSF18); ICOS (CD278); ICOS Ligand (also called B7-H2); HVEM (also called TNFRSF14); DR3; CD28; CD30; CD30L (TNFSF8); TL1A; Nectin-2 (CD112); CD40; CD96; IL-2R (CD122); and CD155 (also called PVR).

An "effective amount" (effective amount of β-alethine and/or a second compound, including but not limited to an immune modulator or an antibody): refers to an amount of a binding agent, an antibody, polypeptide, polynucleotide, small organic molecule, or other drug effective to "treat" a disease or disorder in a subject or mammal. In the case of cancer, the therapeutically effective amount of a drug (e.g., β-alethine, an immune modulator, or an antibody) has a therapeutic effect and as such can reduce the number of cancer cells; decrease tumorigenicity, tumorigenic frequency or tumorigenic capacity; reduce the number or frequency of cancer stem cells; reduce the tumor size; reduce the cancer cell population; inhibit and/or stop cancer cell infiltration into peripheral organs including, for example, the spread of cancer into soft tissue and bone; inhibit and/or stop tumor or cancer cell metastasis; inhibit and/or stop tumor or cancer cell growth; relieve to some extent one or more of the symptoms associated with the cancer; reduce morbidity and mortality; improve quality of life; or a combination of such effects. To the extent the agent (e.g., β-alethine, an immune modulator, or an antibody) prevents growth and/or kills existing cancer cells, it can be referred to as cytostatic and/or cytotoxic.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

As used herein, the term "ex vivo" refers to a condition applied to a cell, a tissue, or other sample obtained from an organism that takes place outside of the organism. For example, an ex vivo treatment of CD8+ T cells can include exposing CD8+ T cells isolated from a sample obtained from a subject to β-alethine in an artificial environment outside the subject.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability ("CDR grafted") (Jones et al., 1986, *Nature*, 321:522-525; Riechmann et al., 1988, *Nature*, 332:323-327; Verhoeyen et al., 1988, *Science*, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539, Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

The term "immune cells" refers to cells of lymphoid or hematopoietic origin and that play a role in the immune response. Immune cells include all thymus-derived and myeloid-derived cells such as lymphocytes (e.g., B cells and T cells), natural killer cells, and myeloid cells (e.g., monocytes, macrophages, dendritic cells, eosinophils, mast cells, basophils, and granulocytes). Immune cells further includes cells with similar functions such as microglia.

An "immune cell sample," as used herein, is a cell sample that comprises immune cells. The immune cell sample can be obtained from primary and secondary lymphoid organs (e.g., thymus, bone marrow, lymph nodes, spleen, tonsils, or mucous membranes of the bowel), blood, a cancer, a cancer region, or a tumor. An immune cell sample includes cell samples in which immune cell subsets have been enriched. Techniques for enriching immune cell subsets from blood or organ tissue are known in the art and include techniques such as flow cytometry, density centrifugation, and magnetic isolation (see, e.g., Salvagno, C. and de Visser, K. E. Methods Mol Biol. 2016; 1458:125-35, which is incorporated by reference in its entirety).

An "immune modulator" as used herein is any molecule that modulates or alters the immune system including but not limited to cytokines, chemokines, complement molecules and numerous drugs. This includes but is not limited to stimulatory or inhibitory immune checkpoint inhibitor (CI or ICI) drugs that promote or reduce the expansion, survival, differentiation, recruitment, function or activity of immune cells of any type including but not limited to CD4+ or CD8+ T cells. The immune modulator may promote the expansion, survival, differentiation, or activity of immune cells by mechanisms including, but not limited to, boosting the generation of tumor-reactive effector T cells or inhibiting Treg cell function to alleviate immunosuppression in the tumor microenvironment (See, e.g., Linch, S. N. et al. Front Oncol. 2015 Feb. 16; 5:34, which is incorporated by reference in its entirety).

The immune modulators include those that function as antagonists of inhibitory immune checkpoint molecules or as agonists of co-stimulatory immune checkpoint molecules. Thus, the immune modulators include antibodies, antibody fragments, drugs or ligands that bind to an inhibitory immune checkpoint molecule and antagonize the activity of the inhibitory immune checkpoint molecule. The immune modulators also include antibodies, antibody fragments, drugs or ligands that bind to a co-stimulatory immune checkpoint molecule and activate (agonistic activity) the co-stimulatory immune checkpoint molecule.

An "inhibitory immune checkpoint molecule," as used herein, includes both receptors and ligands that function as an immune checkpoint. Inhibitory immune checkpoint molecules are negative regulatory molecules that inhibit immune cell function (e.g., inhibit T cell proliferation and cytokine production). Inhibitory immune checkpoint molecules include, but are not limited to, PD1 (also called PDCD1 or CD279); PD-L1 (also called B7-H1 or CD274); PD-L2 (also called B7-DC or CD273); CTLA-4 (also called CD152); B7-H3 (also called CD276); B7-H4 (also called B7S1 or B7x); CD66a (CEACAM1); VISTA (also called B7-H5 or GI24); BTLA; CD160; LAG3 (also called CD223 or Lymphocyte activation gene 3); Indoleamine 2,3-dioxygenase (also called IDO); Galectin-9 (also called LGALS9); TIM-3 (also called HAVCR2); 2B4 (also called CD244);

SIRP alpha (also called CD172a); CD39; CD47; CD48 (also called SLAMF2); A2AR; KIRs; and TIGIT (also called VSTM3).

The term "immune checkpoint" refers to an immune regulatory mechanisms that decreases or increases immune function for instance to prevents the immune system from attacking its own body or to allow an effective anti-virus or anti-cancer response. Immune checkpoint receptors are present on immune cells, and interact with ligands expressed on other immune cells or other types of cells including but not limited to cancer cells. Typically T cells recognize an antigen presented on the MHC molecule and are activated to generate an immune reaction. The activation of T cells is controlled by an interaction between stimulatory and inhibitory immune checkpoint receptors and ligands that occurs in parallel. Immune checkpoint receptors include co-stimulatory receptors and inhibitory receptors, and the T cell activation and the immune reaction are controlled by a balance between a variety of molecules and molecular pairs.

The terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double stranded (duplex). Duplex nucleic acids may be homoduplex or heteroduplex.

PD-1 refers to a predominantly immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GENBANK® Accession No. U64863. For molecules that regulate PD-1, see, e.g., U.S. Pat. No. 8,168,757 B2 and U.S. Pat. No. 9,683,048 B2, each of which is incorporated by reference in their entireties.

PD-L1 is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GENBANK® Accession No. Q9NZQ7.

A "pharmaceutical composition" refers to a composition comprising an excipient, carrier, or adjuvant that can be administered to a subject, together with at least one agent of the present disclosure, and which does not destroy the pharmacological activity thereof and is non-toxic when administered in doses sufficient to deliver a therapeutic effect. In general, those of skill in the art and the U.S. FDA consider a pharmaceutically composition to contain inactive ingredients of any formulation.

As used herein, a "pharmaceutically acceptable carrier" of use is conventional. *Remington's Pharmaceutical Sciences*, by E. W. Martin, Mack Publishing Co., Easton, Pa., 19th Edition, 1995, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (such as powder, pill, tablet, or capsule forms), conventional non-toxic solid carriers may include, for example, pharmaceutical grades of mannitol, lactose, starch, or magnesium stearate. In addition to biologically neutral carriers, pharmaceutical compositions to be administered may contain minor amounts of non-toxic auxiliary substances, such as wetting or emulsifying agents, preservatives, and pH buffering agents and the like, for example sodium acetate or sorbitan monolaurate.

A "pharmaceutical kit" as used herein comprises one or more compartments, one compartment comprising β-alethine and another compartment comprising an immune modulator, wherein the immune modulator is an antagonist of an inhibitory immune checkpoint molecule or an agonist of a stimulatory immune checkpoint molecule.

As used herein, the term "polynucleotide" refers to a polymer of ribonucleic acid (RNA) or deoxyribonucleic acid (DNA). A polynucleotide is made up of four bases; adenine, cytosine, guanine, and thymine/uracil (uracil is used in RNA). A coding sequence from a nucleic acid is indicative of the sequence of the protein encoded by the nucleic acid. The term includes various modifications and analogues known in the art.

"Potentiating" or "potentiatingly" (e.g., a potentiatingly effective amount) refers to an amount of a binding agent, an antibody, polypeptide, polynucleotide, small organic molecule, or other drug, effective to make more effective, or activate a response to a treatment of a disease or disorder in a subject or mammal. In the case of cancer, the potentiatingly effective amount of a drug (e.g., β-alethine, an immune modulator, or an antibody) has a therapeutic effect to increase the power or effect of the drug and as such can reduce the number of cancer cells; decrease tumorigenicity, tumorigenic frequency or tumorigenic capacity; reduce the number or frequency of cancer stem cells; reduce the tumor size; reduce the cancer cell population; inhibit and/or stop cancer cell infiltration into peripheral organs including, for example, the spread of cancer into soft tissue and bone; inhibit and/or stop tumor or cancer cell metastasis; inhibit and/or stop tumor or cancer cell growth; relieve to some extent one or more of the symptoms associated with the cancer; reduce morbidity and mortality; improve quality of life; or a combination of such effects.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component.

"Predetermined value" refers to a laboratory value used as a reference for values/data obtained by laboratory examinations of patients or samples collected from patients. The predetermined value can be an absolute value; a relative value; a value that has an upper and/or lower limit; a range of values; an average value; a median value, a mean value, or a value as compared to a particular control or baseline value. A predetermined value can be based on an individual sample value, such as, for example, a value obtained from a sample from the subject being tested, but at an earlier point in time. The predetermined value can be based on a large number of samples, such as from a population of subjects of the chronological age matched group, or based on a pool of samples including or excluding the sample to be tested.

The term "recombinant" with reference to a nucleic acid or polypeptide refers to one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide may also refer to a polypeptide that has been made using recombinant nucleic acids, including recombinant nucleic acids transferred to a host organism that is not the natural source of the polypeptide.

As used herein, the term "subject" includes any human or nonhuman animal. The term "nonhuman animal" includes, but is not limited to, vertebrates such as nonhuman primates, sheep, dogs, cats, rabbits, ferrets, rodents such as mice, rats and guinea pigs, avian species such as chickens, amphibians, and reptiles. In preferred embodiments, the subject is a mammal such as a nonhuman primate, sheep, dog, cat, rabbit, ferret or rodent. In more preferred embodiments, the subject is a human. The terms, "subject," "patient" and "individual" are used interchangeably herein.

The combination therapy described herein can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the compounds are administered or delivered sequentially, e.g., by different injections in separate syringes.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect may be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed. In certain embodiments disclosed herein, "treatment" leads to long-term resistance to tumor growth, even in the presence of additional stimuli.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The description may use the terms "embodiment" or "embodiments," which may each refer to one or more of the same or different embodiments.

II. Compositions Comprising β-Alethine a. β-Alethine

Disclosed herein are compositions comprising beta alethine (also called β-alethine; beta-alanyl cysteamine disulfide; Betathine™; Beta LT™; BLT; BA; and BT). As indicated above, β-alethine has the following structure:

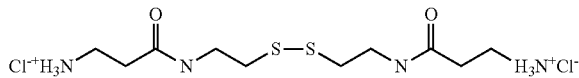

β-alethine is a dimer composed of two small thiols and has diverse biological activity, including potent antitumor activity in vivo. Treatment with β-alethine was shown to increase the percent survival in the Cloudman S-91-DBA/2 model in which melanomas had already been established. See U.S. Pat. No. 5,643,966; see also U.S. Pat. Nos. 6,046, 241 and 6,245,561. β-alethine has been used as an adjunct to chemotherapy in two aggressive murine tumor models, where it was administered along with melphalan in the treatment of the MOPC-315 myeloma and with cyclophosphamide in the treatment of the B16 melanoma. See WO/1999/042099.

β-alethine and certain other thiols and disulfides (described in U.S. Pat. No. 6,007,819, which is incorporated by reference in its entirety) have also been used as adjuvants in vaccines and as immunostimulatory molecules. Further, the compounds beta-alanyl taurine and carbobenzoxy beta-alanyl taurine (Taurox™) and related compounds have been used as anti-cancer agents (see U.S. Pat. Nos. 5,370,818 and 5,578,313, both of which are incorporated by reference in their entireties), for the therapeutic treatment of immune diseases (U.S. Publ. No. 2003-0166715 A1, which is incorporated by reference in its entirety); and in cell culture and therapy (U.S. Pat. Nos. 6,096,536 and 6,323,025, both of which are incorporated by reference in their entireties).

β-alethine is stabilized by its acid salts, particularly its hydrogen halide salts, and especially its hydrochloride salts.

Disclosed herein is β-alethine which is capable of treating cancer in a subject as well as treating or preventing infectious disease in a subject.

β-alethine increases expression of cancer inhibitors, including for example tumor necrosis factor-alpha (TNF-α), tumor necrosis factor-beta (TNF-β), lymphotoxin-beta (LT-β), and Interferon gamma (IFNγ). It is a stable and inexpensive molecule that is relatively easy to manufacture. In addition, β-alethine relieves multiple types of immune "exhaustion" and has limited toxicity. Thus, it provides many advantages for therapeutic and diagnostic methods.

Various techniques for the synthesis of β-alethine are described in the literature. See, for example. U.S. Pat. No. 6,414,114 B2, which is hereby incorporated by reference in its entirety. It is preferred that β-alethine for use in the processes of the invention be prepared by processes which ensure purity of product and preferably also maximize yield, for example by the process of the invention comprising coupling N-CBZ-blocked β-alanine to N-hydroxysuccinimide to produce the corresponding active ester, which is then coupled to cystamine prepared by oxidation of cysteamine with hydrogen peroxide; the product, CBZ-blocked β-alethine, is then recovered and deblocked.

In one embodiment, β-alethine is produced by using multiple synthetic and multiple purification steps.

In one embodiment, β-alethine is produced using three synthetic steps and two purification steps. In one embodiment, β-alethine is produced by the following steps. First, activated ester from N-Cbz-β-alanine is formed. The N-Cbz-/β-alanine activated ester is taken directly to the next step in solution instead of being isolated. Second, the activated ester (from step 1) is coupled to cystamine dihydrochloride. The resulting product compound is N,N'-bis-Cbz-β-alethine. Third, the Cbz groups are removed from N,N'-bis-Cbz-β-alethine using hydrogen bromide (HBr)/acetic acid (AcOH). The resulting compound is β-alethine TM-2HBr (β-alethine hydrobromide salt). Fourth, ion-exchange chromatography is used to exchange the Br ion on β-alethine-2HBr for a Cl ion and to remove non-ionic organic impurities. The resulting purified compound, β-alethine, is precipitated using acetone and water.

b. Immune Modulators

Also disclosed herein are immune modulators for combined treatment of cancer in a subject with β-alethine. The immune modulators promote the expansion, survival, differentiation, recruitment, or activity of immune cells.

In some embodiments, the immune modulator is an antagonist (i.e., inhibits or blocks the activity) of an inhibitory immune checkpoint molecule include, but are not limited to, PD1 (also called PDCD1 or CD279); PD-L1 (also called B7-H1 or CD274); PD-L2 (also called B7-DC or CD273); CTLA-4 (also called CD152); B7-H3 (also called CD276); B7-H4 (also called B7S1 or B7x); CD66a (CEACAM1); VISTA (also called B7-H5 or GI24); BTLA; CD160; LAG3 (also called CD223 or Lymphocyte activation gene 3); Indoleamine 2,3-dioxygenase (also called IDO); Galectin-9 (also called LGALS9); TIM-3 (also called HAVCR2); 2B4 (also called CD244); SIRP alpha (also called CD172a); CD39; CD47; CD48 (also called SLAMF2); A2AR; KIRs; and TIGIT (also called VSTM3).

PD-1 (also called programmed cell death 1 protein; PDCD1; and CD279), a type I membrane protein, is an immune checkpoint molecule that guards against autoimmunity through a dual mechanism of promoting apoptosis (programmed cell death) in antigen specific T-cells in lymph nodes while simultaneously reducing apoptosis in regulatory T cells (anti-inflammatory, suppressive T cells). See, e.g., U.S. Pat. No. 8,168,757 B2 and U.S. Pat. No. 9,683,048 B2, each of which is incorporated by reference in their entireties. PD-1 has two ligands, PD-L1 and PD-L2. Triggering PD-1, expressed on monocytes and up-regulated upon monocytes activation, by its ligand PD-L1 induces IL-10 production which inhibits CD4 T-cell function. However, overexpression of PD-1 on T cells is one of the indicators of T-cell exhaustion (e.g. in chronic infection or cancer). Thus, therapies such as monoclonal antibodies targeting PD-1 that boost the immune system are being developed for the treatment of cancer and chronic infection.

Initial clinical trial results with IgG4 PD-1 antibody Nivolumab were published in 2010 and was approved in 2014. Nivolumab is approved to treat melanoma, lung cancer, kidney cancer, bladder cancer, head and neck cancer, and Hodgkin's lymphoma. Other drugs that either have recently gained approval or are awaiting approval include, but are not limited to, Keytruda (Pembrolizumab) and Antibody BGB-A317.

PD-L1 (also called PD-1 ligand 1; CD274) is correlated with reduced survival in many types of cancer, including esophageal and pancreatic cancer. Its expression on tumor cells inhibits anti-tumor activity through engagement of PD-1 on effector T cells. See, e.g., U.S. Pat. No. 8,217,149 B2, U.S. Pat. No. 9,212,224 B2, and US-2013/0045202 A1, each of which is incorporated by reference in their entireties. Thus, inhibition of the interaction between PD-1 and PD-L1 (also known as immune checkpoint blockade) can enhance T-cell responses in vitro and mediate preclinical antitumor activity. A PD-L1 inhibitor, atezolizumab, recently was approved for treating bladder cancer. Other anti-PD-L1 inhibitors include, but are not limited to, avelumab and durvalumab.

CTLA-4 (also known as Cytotoxic T lymphocyte associated antigen-4 or CD152) is a protein receptor that, functioning as an immune checkpoint, downregulates immune responses. See e.g., U.S. Pat. No. 6,984,720 B1 and PCT/US1999/030895, both of which is herein incorporated by reference in their entireties. CTLA-4 has been a major and apparently highly effective approach in the treatment and/or eradication of a variety of highly malignant forms of cancers.

IDO (Indoleamine-pyrrole 2,3-dioxygenase or INDO EC 1.13.11.52) is a heme-containing immune checkpoint molecule that functions as an immunomodulatory enzyme produced by immunoregulatory cells. See, e.g., U.S. Pat. No. 9,675,571 B2, US-2016/0060237 A1, and US-2013/0177590 A1, all of which are herein incorporated by reference in their entireties. A wide range of human cancers, for example, prostatic, colorectal, pancreatic, cervical, gastric, ovarian, head, lung, etc. overexpress IDO. Some antagonists of IDO, including but not limited to, epacadostat and navoximod (GDC-0919) have been shown to treat cancer.

TIM3 (T-cell immunoglobulin and mucin-domain containing-3, also called Hepatitis A virus cellular receptor 2 or HAVCR2) is a protein that mediates T-cell exhaustion. See, e.g., US-2016.0257749 A1 and WO-2003/063792 A2 both of which are incorporated by reference in their entireties. It is a Th1-specific cell surface protein that regulates macrophage activation and, among other things, enhances the severity of experimental autoimmune encephalomyelitis in mice. The Tim-3 pathway may interact with the PD-1 pathway in the dysfunctional T cells and Tregs in cancer.

LAG3 (Lymphocyte-activation gene 3 or CD223) is a cell surface molecule with diverse biologic effects on T cell function. See, e.g., US-20170101472 A1 and US-2015/0259420 A1, each of which is incorporated by reference in their entireties. It is an immune checkpoint receptor and as such is the target of various drug development programs by pharmaceutical companies seeking to develop new treatments for cancer and autoimmune disorders. The protein negatively regulates cellular proliferation, activation, and homeostasis of T cells, in a similar fashion to CTLA-4 and PD-1 and has been reported to play a role in Treg suppressive function. Soluble LAG (for example IMP321), antibodies that promote an anti-cancer immune response (for example BMS-986016), and antibodies that blunt an autoimmune response (for example GSK283178) are in clinical development.

TIGIT (T cell immunoreceptor with Ig and ITIM domains is an immune receptor present on some T cells and Natural Killer Cells(NK). It is also identified as WUCAM[2] and Vstm3. TIGIT could bind to CD155(PVR) on dendritic cells(DCs), macrophages, etc. with high affinity, and also to CD112(PVRL2) with lower affinity. See, e.g., US-2017/0088613 A1 and US-2016/0355589 A1.

BTLA (B- and T-lymphocyte attenuator or CD272) is an inhibitory receptor whose extracellular domain belongs to the immunoglobulin superfamily. See, e.g., US-2012/0064096 A1 and U.S. Pat. No. 8,563,694 B2, each of which is incorporated by reference in their entireties. Its ligand, herpesvirus entry mediator (HVEM), is a tumor necrosis factor receptor superfamily member. The unique interaction between BTLA and HVEM allows for a system of bidirectional signaling that must be appropriately regulated to balance the outcome of the immune response. BTLA is expressed during activation of T cells, and its activation inhibits the function of human CD8+ cancer-specific T cells.

VISTA, (V-domain Ig suppressor of T cell activation) functions to decrease immune activation (e.g., decrease CD4+ T cell activation and proliferation). See, e.g., US-2017/0051061 A1 and US-2014/0341920 A1, each of which is incorporated by reference in their entireties. VISTA can act as both a ligand and a receptor on T cells to inhibit T cell effector function and maintain peripheral tolerance. It is produced at high levels in tumor-infiltrating lymphocytes, such as myeloid-derived suppressor cells and regulatory T cells, and its blockade with an antibody results in delayed tumor growth. Increase in production of VISTA in monocytes is associated with HIV-infected patients KIRs (Killer-cell immunoglobulin-like receptors) constitute a family of MHC-I binding receptors that plays a major role in regulating the activation thresholds of NK cells and some T cells in humans. See, e.g., US-2016/0272709 A1 and US-2014/0099254 A1, each of which is incorporated by reference in their entireties. Their diversity contributes to the generation of a highly varied NK cell repertoire and aids in blocking NK cell activation and function in a variety of diseases. KIRs mediate an inhibitory signal that decreases NK cell response. Anti-MR antibodies, such as lirlumab (Innate Pharma) and IPH2101 (Innate Pharma) have demonstrated anti-tumor activity in multiple myeloma (Benson et al., 2012, Blood 120:4324-33).

CD39 (Ectonucleoside triphosphate diphosphohydrolase-1 or NTPDase1) is an ectonucleotidase that catalyse the hydrolysis of γ- and β-phosphate residues of triphospho- and diphosphonucleosides to the monophosphonucleoside derivative. See, e.g., US-2013/0273062 A1 and WO 2016/073845 A1, each of which are incorporated by reference in their entireties. It degrades ATP, ADP, and AMP to adenosine; they can be viewed as 'immunological switches' that shift ATP-driven proinflammatory immune cell activity toward an anti-inflammatory state mediated by adenosine. CD39 is highly expressed on the surface of Foxp3+ Tregs and is important for the immunosuppressive activity of Tregs. Expression of CD39 generates an immunosuppressed environment, characterized by increased adenosine levels, which promotes the development and progression of cancer.

In some embodiments, the immune modulator is an agonist of a stimulatory immune checkpoint molecule. Stimulatory immune checkpoint molecules include stimulatory or co-stimulatory immune molecules that can be either receptors and ligands. These include, but are not limited to, OX-40 (also called CD134); CD226 (also called DNAM-1); CD137 (also called 4-1BB); CD40L (also called CD154 or TNFSF5); 4-1BBL (also called CD137L); OX-40L (also called TNFSF4 or CD252); CD27; TNFSF14 (also called LIGHT or CD258); CD70 (also called CD27L or TNFSF7); CD80 (also called B7-1); CD86 (also called B7-2); GITR (CD357); GITR Ligand (also called TNFSF18); ICOS (CD278); ICOS Ligand (also called B7-H2); HVEM (also called TNFRSF14); DR3; CD28; CD30; CD30L (TNFSF8); TL1A; Nectin-2 (CD112); CD40; CD96; IL-2R (CD122); and CD155 (also called PVR).

In some embodiment, the immune modulator is an antibody, antibody fragment, or ligand that binds to the inhibitory immune checkpoint molecule. In some embodiments, the immune modulator is an antibody, antibody fragment, or ligand that binds to the co-stimulatory immune checkpoint molecule. For example, in some embodiments, the agonist of the stimulatory or co-stimulatory immune molecule is a ligand (e.g., OX-40L) that binds to a stimulatory or co-stimulatory receptor. In some embodiments, the agonist is an antibody or antigen binding fragment that binds to and activates a stimulatory or co-stimulatory receptor (e.g., OX40).

In some embodiments, the immune modulator is a ligand selected from the group consisting of CD40L (also called CD154 or TNFSF5); 4-1BBL (also called CD137L); OX-40L (also called TNFSF4 or CD252); CD70 (also called CD27L or TNFSF7); CD80 (also called B7-1); CD86 (also called B7-2); GITR Ligand (also called TNFSF18); ICOS Ligand (also called B7-H2); HVEM (also called TNFRSF14; CD30L (TNFSF8); TL1A; Nectin-2 (CD112); CD40; and CD155 (also called PVR).

In some embodiments, the immune modulator is an anti-PD-1 antibody or antibody fragment; an anti-PD-L1 antibody or antibody fragment; or an anti-CTLA-4 antibody or antibody fragment. In some embodiments, the immune modulator is an anti-OX-40 antibody or antibody fragment. In some embodiments, the immune modulator is a bispecific antibody. In some embodiments, the immune modulator is a trispecific antibody. In some embodiments, the immune modulator is a chimeric antibody, a humanized antibody, a human antibody, or fusion protein comprising an antibody.

ICOS (Inducible T-cell Costimulator or CD278) is an immune checkpoint protein that is expressed on activated. T cells. See, e.g., U.S. Pat. No. 9,193,789 B2 and U.S. Pat. No. 9,738,718 B2, each of which is incorporated by reference in their entireties. ICOS enhances all basic T-cell responses to a foreign antigen, namely proliferation, secretion of lymphokines, upregulation of molecules that mediate cell-cell interaction, and effective help for antibody secretion by B cells.

c. Pharmaceutical Compositions and Pharmaceutically Acceptable Carriers

Disclosed herein is a pharmaceutical composition comprising β-alethine capable of treating cancer in a subject. Also disclosed herein is a pharmaceutical composition comprising β-alethine and an immune modulator disclosed herein capable of treating cancer in a subject.

In some embodiments, the disclosure provides a pharmaceutical composition comprising β-alethine and an immune modulator, wherein the immune modulator is an antagonist of an inhibitory immune checkpoint molecule or an agonist of a stimulatory immune checkpoint molecule. In some embodiments, the immune modulator promotes the expansion, survival, differentiation, recruitment, function, or activity of immune cells.

In some embodiments, the immune modulator of the pharmaceutical composition inhibits or blocks the activity of an inhibitory immune checkpoint molecule selected from the group consisting of: PD1 (also called PDCD1 or CD279); PD-L1 (also called B7-H1 or CD274); PD-L2 (also called B7-DC or CD273); CTLA-4 (also called CD152); B7-H3 (also called CD276); B7-H4 (also called B7S1 or B7x);

CD66a (CEACAM1); VISTA (also called B7-H5 or GI24); BTLA; CD160; LAG3 (also called CD223 or Lymphocyte activation gene 3); Indoleamine 2,3-dioxygenase (also called IDO); Galectin-9 (also called LGALS9); TIM-3 (also called HAVCR2); 2B4 (also called CD244); SIRP alpha (also called CD172a); CD39; CD47; CD48 (also called SLAMF2); A2AR; KIRs; and TIGIT (also called VSTM3). The immune modulator may be a single molecule or a mixture of molecules with these properties. In some embodiments, the immune modulator inhibits or blocks the activity of two inhibitory immune checkpoint molecules. In some embodiments, the immune modulator inhibits or blocks the activity of three inhibitory immune checkpoint molecules. In some embodiments, the immune modulator inhibits or blocks the activity of four inhibitory immune checkpoint molecules. In some embodiments, the immune modulator inhibits or blocks the activity of more than four inhibitory immune checkpoint molecules.

In one embodiment, the immune modulator is an anti-PD-1 antibody or antibody fragment thereof. In one embodiment, the immune modulator is an anti-PD-L1 antibody or antibody fragment thereof. In one embodiment, the immune modulator is an anti-CTLA-4 antibody or antibody fragment thereof.

In some embodiments, the immune modulator is an antibody, antibody fragment, or ligand that binds to the co-stimulatory immune checkpoint molecule. The immune modulator may be a single molecule or a mixture of molecules with these properties. In some embodiments, the immune modulator is an agonist of the co-stimulatory immune checkpoint molecule selected from the group consisting of: OX-40 (also called CD134); CD226 (also called DNAM-1); CD137 (also called 4-1BB); CD40L (also called CD154 or TNFSF5); 4-1BBL (also called CD137L); OX-40L (also called TNFSF4 or CD252); CD27; TNFSF14 (also called LIGHT or CD258); CD70 (also called CD27L or TNFSF7); CD80 (also called B7-1); CD86 (also called B7-2); GITR (CD357); GITR Ligand (also called TNFSF18); ICOS (CD278); ICOS Ligand (also called B7-H2); HVEM (also called TNFRSF14); DR3; CD28; CD30; CD30L (TNFSF8); TL1A; Nectin-2 (CD112); CD40; CD96; IL-2R (CD122); and CD155 (also called PVR). In one embodiment, the immune modulator is an anti-OX-40 antibody or antibody fragment thereof.

In some embodiments, the pharmaceutical composition comprises an excipient, carrier, or adjuvant that can be administered to a subject, together with β-alethine and/or an immune modulator as disclosed herein, and which does not destroy the pharmacological activity thereof and is non-toxic when administered in doses sufficient to deliver a therapeutic effect. (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN. In general, those of skill in the art and the U.S. FDA consider a pharmaceutically composition to contain inactive ingredients of any formulation.

Pharmaceutical compositions described herein can be useful in enhancing, inducing, or activating an immune activity and treating a condition, such as a cancer as disclosed herein. Examples of cancer that can be treated in accordance with the pharmaceutical compositions or pharmaceutically acceptable carriers or formulations described herein include, but are not limited to, B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), myelodysplasia, neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia. In one embodiment, examples of cancer that can be treated in accordance with the methods described herein include, but are not limited to, advanced, recurrent, or metastatic solid tumor, lymphoma (e.g., diffuse large B-cell lymphoma or burkitt's lymphoma), breast cancer, prostate cancer, head & neck cancer, colorectal cancer, colon cancer, melanoma (e.g., metastatic melanoma), endometrial cancer, renal cell carcinoma, renal clear cell carcinoma, lung cancer (e.g., non-small cell lung cancer or lung adenocarcinoma), ovarian cancer, gastric cancer, bladder cancer, stomach cancer, uterine cancer, pheochromocytoma, metastatic cutaneous squamous cell carcinoma (e.g., in transplantation patients), merkel cell carcinoma, cutaneous T-cell lymphoma, neuro-endocrine tumor, tumor of bone origin (e.g., osteosarcoma), hemangiopericytoma, tumor related to genetic syndromes (NF1 or VHL), chordoma, ependymoma, medulloblastoma, germinoma, tumor of small intestine, appendiceal cancer, and viral related tumor (e.g., Kaposi's sarcoma, head and neck cancer, cervical cancer, lymphoma). The pharmaceutical compositions described herein are in one embodiment for use as a medicament or diagnostic. The pharmaceutical compositions and pharmaceutically acceptable carriers or formulations that comprise β-alethine described herein are in one embodiment for use in a method for the treatment of cancer or infectious diseases. This disclosure includes treating and preventing conditions often called "pre-cancers", dysplasias, or high risk lesions.

The term "pre-cancer" is used herein to refer to cells that are not presently cancerous, but are likely to develop into tumor forming cells. "Pre-cancerous" or "abnormal precancerous" samples refer to samples that exhibit mild to severe dysplasia. A "premalignant lesion", as used herein refers to benign tissue that has the potential of malignant transformation. Cytologically adenomas show varying degrees of dysplasia ranging from mild to severe.

The cytological states are morphologically defined herein by the criteria used to determine cell morphology using methods known in the art (e.g., Papanicalou-stained ("PAP-stain") cytology). Examples of states of a pre-cancerous cell are classified herein as (1) normal (no significant abnormalities), (2) metaplasia (squamous metaplasia), (3) mild dysplasia (squamous atypia), (4) moderate dysplasia (squamous atypia), (5) severe dysplasia (marked squamous atypia).

In some embodiments, the compositions are sterile. Sterility is readily accomplished by filtration through, e.g., sterile filtration membranes, known in the art.

III. Methods of Use a. Therapeutic Uses and Methods

The present disclosure provides therapeutic uses and methods to treat disease using the pharmaceutical compositions disclosed herein. In diseases disclosed herein, checkpoint inhibitor molecules are dysregulated. The therapeutic uses and methods disclosed herein comprise treatment that regulate checkpoint inhibitor expression or function. Without being bound by theory, diseases treated herein include cancer and infectious disease.

i. Cancer

Also disclosed herein are methods of treating cancer in a subject in need thereof, which comprises administering to the subject an effective amount of a combination of β-alethine and an immune modulator, wherein the immune modulator is an antagonist of an inhibitory immune checkpoint molecule or an agonist of a stimulatory immune checkpoint molecule. In some embodiments, administration of β-alethine occurs before administration of the immune modulator. In some embodiments, administration of β-alethine occurs concurrently with administration of the immune modulator. In some embodiments, administration of β-alethine occurs after administration of the immune modulator. In some embodiments, the immune modulator promotes the expansion, survival, differentiation, recruitment, function, or activity of immune cells. In some embodiments, the immune modulator promotes the expansion, survival, differentiation, recruitment, function, or activity of CD4+ or CD8+ T cells. In some embodiments the immune modulator(s) and/or the β-alethine may be given ex vivo.

Also disclosed herein is a method of potentiating the effect of an immune modulator during the treatment or preparation for treatment of cancer in a subject. The method comprises administering to the subject an immune modulator and subsequently administering to said subject a potentiatingly effective amount of β-alethine, wherein the immune modulator is an antagonist of an inhibitory immune checkpoint molecule or an agonist of a stimulatory immune checkpoint molecule. In some embodiments, the immune modulator promotes the expansion, survival, differentiation, recruitment, function, or activity of immune cells. In some embodiments, administration of β-alethine occurs after administration of the immune modulator. In some embodiments, the immune modulator promotes the expansion, survival, differentiation, recruitment, function, or activity of CD4+ or CD8+ T cells.

Also disclosed herein is a method of inhibiting tumor growth in a subject having cancer, the method comprising injecting an effective amount of β-alethine into the tumor of the subject. In some embodiments, the method provides wherein β-alethine is injected into the tumor of the subject before, concurrently with, or after the administration of an immune modulator to the subject, wherein the immune modulator is an antagonist of an inhibitory immune checkpoint molecule or an agonist of a stimulatory immune checkpoint molecule. In some embodiments, the immune modulator promotes the expansion, survival, differentiation, recruitment, function, or activity of immune cells. In some embodiments, the immune modulator promotes the expansion, survival, differentiation, recruitment, function, or activity of CD4+ or CD8+ T cells or a decrease in inhibitory function such as exerted by MDSCs and inflammatory macrophages.

In some embodiments, the method of treating cancer, the method of potentiating the effect of an immune modulator during the treatment of cancer, or the method of inhibiting tumor growth comprises administering β-alethine with an immune modulator that is an antagonist of an inhibitory immune checkpoint molecule. In some embodiments, the immune modulator inhibits or blocks the activity of an inhibitory immune checkpoint molecule selected from the group consisting of: PD1 (also called PDCD1 or CD279); PD-L1 (also called B7-H1 or CD274); PD-L2 (also called B7-DC or CD273); CTLA-4 (also called CD152); B7-H3 (also called CD276); B7-H4 (also called B7S1 or B7x); CD66a (CEACAM1); VISTA (also called B7-H5 or GI24); BTLA; CD160; LAG3 (also called CD223 or Lymphocyte activation gene 3); Indoleamine 2,3-dioxygenase (also called IDO); Galectin-9 (also called LGALS9); TIM-3 (also called HAVCR2); 2B4 (also called CD244); SIRP alpha (also called CD172a); CD39; CD47; CD48 (also called SLAMF2); A2AR; KIRs; and TIGIT (also called VSTM3).

In some embodiments, the immune modulator is an antibody, antibody fragment, or ligand that binds to the inhibitory immune checkpoint molecule. In some embodiments, the immune modulator is an anti-PD-1 antibody or antibody fragment thereof, an anti-PD-L1 antibody or antibody fragment thereof, or an anti-CTLA-4 antibody or antibody fragment thereof.

In some embodiments, the method of treating cancer, the method of potentiating the effect of an immune modulator during the treatment of cancer, or the method of inhibiting tumor growth comprises administering β-alethine with an immune modulator that is an agonist of a co-stimulatory immune checkpoint molecule. In some embodiments, the immune modulator of the methods described herein is an agonist of a co-stimulatory molecule selected from the group consisting of: OX-40 (also called CD134); CD226 (also called DNAM-1); CD137 (also called 4-1BB); CD40L (also called CD154 or TNFSF5); 4-1BBL (also called CD137L); OX-40L (also called TNFSF4 or CD252); CD27; TNFSF14 (also called LIGHT or CD258); CD70 (also called CD27L or TNFSF7); CD80 (also called B7-1); CD86 (also called B7-2); GITR (CD357); GITR Ligand (also called TNFSF18); ICOS (CD278); ICOS Ligand (also called B7-H2); HVEM (also called TNFRSF14); DR3; CD28; CD30; CD30L (TNFSF8); TL1A; Nectin-2 (CD112); CD40;

CD96; IL-2R (CD122); and CD155 (also called PVR). In some embodiments, the immune modulator of the methods described herein is an anti-OX-40 antibody or antibody fragment thereof.

Also disclosed herein is a method of treating cancer in a subject in need thereof, which comprises: (i) identifying a subject with an immune cell or cancer cell sample that has an expression level of an inhibitory immune checkpoint molecule higher than a predetermined value, and (ii) administering to said subject an effective amount of β-alethine.

Also disclosed herein is a method of treating cancer in a subject in need thereof, which comprises: (i) identifying a subject with an immune cell or cancer cell sample that has an expression level of a stimulatory immune checkpoint molecule lower than a predetermined value, and (ii) administering to said subject an effective amount of β-alethine.

Also disclosed herein is a method of treating cancer in a subject in need thereof, the method comprising the steps of (i) detecting the expression level of an inhibitory checkpoint molecule in an immune cell or cancer cell sample from the subject; and (ii) if the expression level is higher than a predetermined value, administering an effective amount of β-alethine to the subject.

Also disclosed herein is a method of treating cancer in a subject in need thereof, the method comprising the steps of (i) detecting the expression level of a stimulatory molecule in an immune cell or cancer cell sample from the subject; and (ii) if the expression level is lower than a predetermined value, administering an effective amount of β-alethine to the subject.

Also disclosed herein is a method of treating cancer in a subject in need thereof, the method comprising the steps of (i) determining whether ex vivo treatment of an immune cell or cancer cell sample from the subject with β-alethine reduces the expression level of an inhibitory immune checkpoint molecule; and if so (ii) administering an effective amount of β-alethine to the subject.

Also disclosed herein is a method of treating cancer in a subject in need thereof, the method comprising the steps of (i) determining whether ex vivo treatment of an immune cell or cancer cell sample from the subject with β-alethine increases the expression level of stimulatory immune checkpoint molecule; and if so (ii) administering an effective amount of β-alethine to the subject.

Also disclosed herein is a method of determining the efficacy of β-alethine therapy for the treatment of cancer in a subject in need thereof, the method comprising the steps of: (i) detecting the expression level of an inhibitory immune checkpoint molecule in an immune cell or cancer cell sample from the subject; (ii) wherein an expression level higher than a predetermined value indicate that the subject is likely to respond favorably to β-alethine therapy. In another embodiment, the method further comprises the step of administering an effective amount of β-alethine to the subject if the expression level of the inhibitory checkpoint molecule in the immune cell or cancer cell sample are higher than the predetermined value.

Also disclosed herein is a method of determining the efficacy of β-alethine therapy for the treatment of cancer in a subject in need thereof, the method comprising the steps of: (i) detecting the expression level of a stimulatory immune checkpoint molecule in an immune cell or cancer cell sample from the subject; (ii) wherein an expression level lower than a predetermined value indicate that the subject is likely to respond favorably to β-alethine therapy. In another embodiment, the method further comprises the step of administering an effective amount of β-alethine to the subject if the expression level of the stimulator immune checkpoint molecule in the immune cell or cancer cell sample are lower than the predetermined value.

Also disclosed herein is a method of predicting the efficacy of β-alethine therapy for the treatment of cancer in a subject in need thereof, the method comprising determining whether ex vivo treatment, or initial in vivo treatment of an immune cell or cancer cell sample from the subject with β-alethine significantly reduces the expression level of an inhibitory checkpoint molecule, wherein reduced expression of the inhibitory checkpoint molecule indicates that the subject is likely to respond favorably to β-alethine therapy. In another embodiment, the method further comprises the step of administering an effective amount of β-alethine to the subject if the ex vivo treatment or initial in vivo treatment of the immune cell or cancer cell sample with β-alethine significantly reduced expression of the inhibitory checkpoint molecule.

Also disclosed herein is a method of predicting the efficacy of β-alethine therapy for the treatment of cancer in a subject in need thereof, the method comprising determining whether ex vivo treatment, or initial in vivo treatment of an immune cell or cancer cell sample from the subject with β-alethine increases the expression level of a stimulatory immune checkpoint molecule, wherein increased expression of the stimulatory immune checkpoint molecule indicates that the subject is likely to respond favorably to β-alethine therapy. In another embodiment, the method further comprises the step of administering an effective amount of β-alethine to the subject if the ex vivo treatment or initial in vivo treatment of the immune cell or cancer cell sample with β-alethine increased expression of the stimulatory immune checkpoint molecule.

Also disclosed herein is a method of predicting the efficacy of β-alethine therapy for the treatment of cancer in a subject in need thereof, the method comprising (a) administering an effective amount of a pharmaceutical compositions comprising β-alethine and/or an immune modulator disclosed herein; and (b) measuring ex vivo or initial in vivo treatment whether administering the pharmaceutical composition reduces the expression level of an inhibitory checkpoint molecule, wherein reduced expression of the inhibitory checkpoint molecule indicates that the subject is likely to respond or has responded favorably to β-alethine therapy. In another embodiment, the method further comprises an additional step of administering an effective amount of β-alethine to the subject if the ex vivo treatment of the immune cell or cancer cell sample with β-alethine reduced expression of the inhibitory checkpoint molecule.

Also disclosed herein is a method of predicting the efficacy of β-alethine therapy for the treatment of cancer in a subject in need thereof, the method comprising (a) administering an effective amount of a pharmaceutical compositions comprising β-alethine and/or an immune modulator disclosed herein; and (b) measuring ex vivo or initial in vivo treatment whether administering the pharmaceutical composition increases the expression level of a stimulatory checkpoint molecule, wherein increased expression of the stimulatory immune checkpoint molecule indicates that the subject is likely to respond or has responded favorably to β-alethine therapy. In another embodiment, the method further comprises an additional step of administering an effective amount of β-alethine to the subject if the ex vivo treatment of the immune cell or cancer cell sample with β-alethine increased expression of the stimulatory checkpoint molecule.

In some embodiments, the inhibitory checkpoint molecule is selected from the group consisting of: PD1 (also called PDCD1 or CD279); PD-L1 (also called B7-H1 or CD274); PD-L2 (also called B7-DC or CD273); CTLA-4 (also called CD152); B7-H3 (also called CD276); B7-H4 (also called B7S1 or B7x); CD66a (CEACAM1); VISTA (also called B7-H5 or GI24); BTLA; CD160; LAG3 (also called CD223 or Lymphocyte activation gene 3); Indoleamine 2,3-dioxygenase (also called IDO); Galectin-9 (also called LGALS9); TIM-3 (also called HAVCR2); 2B4 (also called CD244); SIRP alpha (also called CD172a); CD39; CD47; CD48 (also called SLAMF2); A2AR; KIRs; and TIGIT (also called VSTM3).

In some embodiments, the co-stimulatory checkpoint molecule is selected from the group consisting of: OX-40 (also called CD134); CD226 (also called DNAM-1); CD137 (also called 4-1BB); CD40L (also called CD154 or TNFSF5); 4-1BBL (also called CD137L); OX-40L (also called TNFSF4 or CD252); CD27; TNFSF14 (also called LIGHT or CD258); CD70 (also called CD27L or TNFSF7); CD80 (also called B7-1); CD86 (also called B7-2); GITR (CD357); GITR Ligand (also called TNFSF18); ICOS (CD278); ICOS Ligand (also called B7-H2); HVEM (also called TNFRSF14); DR3; CD28; CD30; CD30L (TNFSF8); TL1A; Nectin-2 (CD112); CD40; CD96; IL-2R (CD122); and CD155 (also called PVR).

In some embodiments, the expression level determined is the mRNA expression level. In another embodiment, the expression level determined is the cell surface expression level.

In some embodiments, the immune cell or cancer cell sample is a cancer cell sample obtained from a cancer, a cancer region, a tumor, lymph, bone marrow, body fluid, or blood. In one embodiment, the immune cell or cancer cell sample is an immune cell sample obtained from a cancer, a cancer region, lymph, bone marrow, a tumor, body fluid or blood.

In another embodiment, subjects with stable cancer or shrinking tumors are treated with the composition disclosed herein. In some embodiments, subjects with cancer are treated to minimize residual disease, sub-clinical cancer, or to move from a high risk of recurrence situation to one of immunity and reduced risk of recurrence.

The amount of an antibody or composition (e.g., which will be effective in the treatment) of a condition will depend on the nature of the disease and can be determined by standard clinical techniques.

The precise dose to be employed in a composition will also depend on the route of administration, and the seriousness of the disease, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human animals including mammals and transgenic mammals can also be treated. Treatment dosages are optimally titrated to optimize safety and efficacy.

As provided herein, a composition comprising β-alethine and/or an immune modulator can be administered at a particular dose and/or at particular timing intervals. For the treatment of a disease disclosed herein, the appropriate dosage of the composition of the present invention depends on, for example, the type of disease to be treated, the severity and course of the disease, the responsiveness of the disease, whether the composition is administered for therapeutic or preventative purposes, previous therapy, patient's clinical history, all at the discretion of the treating physician. The composition can be administered one time or over a series of treatments lasting from several days to several months, or until a cure is effected or a diminution of the disease state is achieved (e.g., reduction in tumor size). In order to prevent re-occurrence or a second similar cancer therapy may be given continuously or periodically throughout a subject's life. Optimal dosing schedules can be calculated from measurements of drug accumulation in the body of the patient and will vary depending on the relative potency of an individual pharmaceutical composition. The administering physician can easily determine optimum dosages, dosing methodologies and repetition rates.

In certain embodiments, dosage of β-alethine is from 10 ng to 100 mg per kg of body weight, and can be given once or more daily, weekly, monthly or yearly. In certain embodiments, the dosage of β-alethine and/or the immune modulator is from about 30 ng to about 30 mg per kg of body weight and is given every week. In certain embodiments, β-alethine and/or the immune modulator is given once every week. In certain embodiments, β-alethine is given once every week, every two weeks, or once every three weeks. The treating physician can estimate repetition rates for dosing based on the longevity of the effect on the immune cells.

In certain embodiments, dosage of the immune modulator is from 10 μg to 100 mg per kg of body weight, and can be given once or more daily, weekly, monthly or yearly. In certain embodiments, the dosage of the immune modulator is from about 1 mg to about 50 mg per kg of body weight. In certain embodiments, the immune modulator is given once every week. In certain embodiments, the immune modulator is given once every two weeks or once every three weeks. The treating physician can estimate repetition rates for dosing based on measured residence times and concentrations of the drug in bodily fluids or tissues.

In some embodiments, the methods disclosed herein provide administering β-alethine to the subject before the administration of an immune modulator to the subject. In some embodiments, administration of β-alethine occurs 1 hour, 2, hours, 3, hours, 4 hours, 5, hours, 6 hours, 7 hours, 8 hours, 9 hours, 10 hours, 11 hours, 12 hours, 18 hours, 24 hours, 2 days, 3 days, 4 days, 5 days, 6 days, 7 days, 8 days, 9 days, 10 days, 11 days, 12 days, 13 days, 2 weeks, 3 weeks, 4 weeks, 2 months, or 3 months before the administration of an immune modulator to the subject.

In some embodiments, the methods disclosed herein provide administering β-alethine to the subject concurrently with the administration of an immune modulator to the subject.

In some embodiments, the methods disclosed herein provide administering β-alethine to the subject after the administration of an immune modulator to the subject. In some embodiments, administration of β-alethine occurs 1 hour, 2, hours, 3, hours, 4 hours, 5, hours, 6 hours, 7 hours, 8 hours, 9 hours, 10 hours, 11 hours, 12 hours, 18 hours, 24 hours, 2 days, 3 days, 4 days, 5 days, 6 days, 7 days, 8 days, 9 days, 10 days, 11 days, 12 days, 13 days, 2 weeks, 3 weeks, 4 weeks, 2 months, or 3 months after the administration of an immune modulator to the subject.

In some embodiments, a subject is administered multiple doses of β-alethine before a single dose of an immune modulator. In some embodiments, a subject is administered multiple doses of β-alethine after a single dose of an immune modulator.

In some embodiments, a subject is administered multiple doses of an immune modulator before a single dose of β-alethine. In some embodiments, a subject is administered multiple doses of an immune modulator after a single dose of β-alethine.

In some embodiments, a subject is administered multiple doses of an immune modulator after multiple doses of β-alethine. In some embodiments, a subject is administered multiple doses of β-alethine after multiple doses of an immune modulator.

In some embodiments, the time between doses of administration of any combination (i.e., between one dose of β-alethine and a second dose of β-alethine; between a first dose of β-alethine and a second dose of an immune modulator; between a first dose of an immune modulator and a second dose of β-alethine; and between one dose of an immune modulator and a second dose of an immune modulator) occurs 1 hour, 2, hours, 3, hours, 4 hours, 5, hours, 6 hours, 7 hours, 8 hours, 9 hours, 10 hours, 11 hours, 12 hours, 18 hours, 24 hours, 2 days, 3 days, 4 days, 5 days, 6 days, 7 days, 8 days, 9 days, 10 days, 11 days, 12 days, 13 days, 2 weeks, 3 weeks, 4 weeks, 2 months, 3 months, 4 months, 5 months 6 months 9 months or a year after the administration of an immune modulator to the subject.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

In some embodiments, subjects with stable cancer or shrinking tumors are treated with the composition disclosed herein. In some embodiments, subjects with cancer are treated to minimize residual disease or to move from a high risk situation to one of immunity and reduced risk of recurrence.

In some embodiments, β-alethine is administered to a patient along with a cancer vaccine. This generation of immunity via this combination is especially important to enhance the effect of vaccines. For example, some recent and experimental vaccines, such as Provenge, which may improve survival, does not eliminate cancer from a patient.

In some embodiments, patients receiving treatment using one or more cancer vaccines also are treated with β-alethine. In some embodiments, the combination therapy of a cancer vaccine and β-alethine is synergistic. In some embodiments, the combination therapy of a cancer vaccine and β-alethine results in immunity from recurrence. In some embodiments, therapy with a cancer vaccine is enhanced by the β-alethine combination methods.

In some embodiments, β-alethine is combined with other cancer therapies to treat a subject diagnosed with cancer or suspected of having cancer or with high risk of developing cancer. In some embodiments, the subject is treated with radiation therapy or chemotherapy. In some embodiments, combination treatment of β-alethine with radiation therapy enhances the immune response and/or leads to permanent immunity. In some embodiments, combination treatment of β-alethine with chemotherapy enhances the immune response and/or leads to permanent immunity.

β-alethine, one or more immune modulators, and/or the pharmaceutical compositions of the present invention are administered in any number of ways for either local or systemic treatment. Administration can be topical such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, intravesicular (i.e., into the bladder), epidermal, and transdermal); oral; or parenteral including intravenous, intraarterial, subcutaneous (s.c.), intra-tumoral (i.t.), intraperitoneal, intradermal, or intramuscular injection or infusion; intracranial (e.g., intrathecal or intraventricular) administration; or administration to a tumor draining lymph node.

In some embodiments, β-alethine is administered to the subject via intravenous, intramuscular, intraperitoneal, intratumoral, subcutaneous, intravesicular, or oral administration. In some embodiments, the immune modulator is administered to the subject via intravenous, intramuscular, intraperitoneal, intratumoral, subcutaneous, or oral administration. In some embodiments, administration or β-alethine and the immune modulator is through the same method (e.g., both are administered intra-tumorally). In some embodiments, administration or β-alethine and the immune modulator is through the different methods (e.g., β-alethine is administered intra-tumorally, and the immune modulator is administered intravenously). In one embodiment, the administration of β-alethine is subcutaneous. In one embodiment, the administration of β-alethine is intra-tumoral (i.t.). In one embodiment, the administration of β-alethine is intra-dermal (i.d.). In one embodiment, the administration of β-alethine is in to the lymph or lymph node. In one embodiment, the administration of immune modulator is subcutaneous. In one embodiment, the administration of immune modulator is intra-tumoral (i.t.). In some embodiments, the administration is through a vaccine.

In one embodiment, the pharmaceutical composition comprising β-alethine can be combined in a pharmaceutical combination formulation, or dosing regimen as combination therapy, with a second compound having anti-cancer properties.

ii. Infectious Disease

The immune system uses the same cells, cytokines and signaling networks to fight both proliferations of foreign organisms (infections) and proliferations of cancer cells. In one embodiment, disclosed herein is a method of treating or preventing an infectious disease in a subject in need thereof, which comprises: (i) identifying a subject with an immune cell sample that has an expression level of an inhibitory immune checkpoint molecule higher than a predetermined value, and (ii) administering to said subject an effective amount of β-alethine.

In one embodiment, disclosed herein is a method of treating or preventing an infectious disease in a subject in need thereof, which comprises: (i) identifying a subject with an immune cell sample that has an expression level of a stimulatory immune checkpoint molecule lower than a predetermined value, and (ii) administering to said subject an effective amount of β-alethine.

In another embodiment, disclosed herein is a method of treating or preventing an infectious disease in a subject in need thereof, the method comprising the steps of: (i) detecting the expression level of an inhibitory immune checkpoint molecule in an immune cell sample from the subject; and (ii)

if the expression level is higher than a predetermined value, administering an effective amount of β-alethine to the subject.

In another embodiment, disclosed herein is a method of treating or preventing an infectious disease in a subject in need thereof, the method comprising the steps of: (i) detecting the expression level of a stimulatory immune checkpoint molecule in an immune cell sample from the subject; and (ii) if the expression level is lower than a predetermined value, administering an effective amount of β-alethine to the subject.

In another embodiment, disclosed herein is a method of treating or preventing an infectious disease in a subject in need thereof, the method comprising the steps of: (i) determining whether ex vivo treatment of an immune cell sample from the subject with β-alethine reduces the expression level of an inhibitory checkpoint molecule; and if so (ii) administering an effective amount of β-alethine to the subject.

In another embodiment, disclosed herein is a method of treating or preventing an infectious disease in a subject in need thereof, the method comprising the steps of: (i) determining whether ex vivo treatment of an immune cell sample from the subject with β-alethine increases the expression level of a stimulatory immune checkpoint molecule; and if so (ii) administering an effective amount of β-alethine to the subject.

In another embodiment, disclosed herein is a method of treating or preventing an infectious disease in a subject in need thereof, the method comprising the steps of: (i) determining whether in vitro treatment of an immune cell sample from the subject with β-alethine reduces the expression level of an inhibitory checkpoint molecule; and if so (ii) administering an effective amount of β-alethine to the subject.

In another embodiment, disclosed herein is a method of treating or preventing an infectious disease in a subject in need thereof, the method comprising the steps of: (i) determining whether in vitro treatment of an immune cell sample from the subject with β-alethine increases the expression level of a stimulatory checkpoint molecule; and if so (ii) administering an effective amount of β-alethine to the subject.

In another embodiment, disclosed herein is a method of determining the efficacy of β-alethine therapy for the treatment or prevention of an infectious disease in a subject in need thereof, the method comprising the steps of: (i) detecting the expression level of an inhibitory immune checkpoint molecule in an immune cell sample from the subject; wherein an expression level higher than a predetermined value indicate that the subject is likely to respond favorably to β-alethine therapy. In another embodiment, the method comprises a further step of administering an effective amount of β-alethine to the subject if the expression level of the inhibitory immune checkpoint molecule in the immune cell sample is higher than the predetermined value.

In another embodiment, disclosed herein is a method of determining the efficacy of β-alethine therapy for the treatment or prevention of an infectious disease in a subject in need thereof, the method comprising the steps of: (i) detecting the expression level of a stimulatory checkpoint molecule in an immune cell sample from the subject; wherein an expression level lower than a predetermined value indicate that the subject is likely to respond favorably to β-alethine therapy. In another embodiment, the method comprises a further step of administering an effective amount of β-alethine to the subject if the expression level of the stimulatory immune checkpoint molecule in the immune cell sample is lower than the predetermined value.

In another embodiment, disclosed herein is a method of determining the efficacy of β-alethine therapy for the treatment of an infectious disease in a subject in need thereof, the method comprising determining whether ex vivo treatment of an immune cell sample from the subject with β-alethine reduces the expression level of an inhibitory immune checkpoint molecule, wherein reduced expression of the inhibitory checkpoint molecule indicates that the subject is likely to respond favorably to β-alethine therapy. In another embodiment, the method comprises a further step of administering an effective amount of β-alethine to the subject if the ex vivo treatment of the immune cell sample with β-alethine reduced expression of the inhibitory immune checkpoint molecule.

In another embodiment, disclosed herein is a method of determining the efficacy of β-alethine therapy for the treatment of an infectious disease in a subject in need thereof, the method comprising determining whether ex vivo treatment of an immune cell sample from the subject with β-alethine increases the expression level of a stimulatory immune checkpoint molecule, wherein increased expression of the stimulatory immune checkpoint molecule indicates that the subject is likely to respond favorably to β-alethine therapy. In another embodiment, the method comprises a further step of administering an effective amount of β-alethine to the subject if the ex vivo treatment of the immune cell sample with β-alethine increased expression of the stimulatory immune checkpoint molecule.

In some embodiments, treatment of an infectious disease includes determining expression level of a marker. In some embodiments, the expression level is determined by measuring expression of mRNA or a protein. In some embodiments, the expression level is the mRNA expression level. In some embodiments, the expression level is the cell surface expression level.

In some embodiments, treatment of an infectious disease includes isolation of an immune cell sample for ex vivo application disclosed herein. In some embodiments, the immune cell sample is obtained from a site of infection or the blood.

In some embodiments, treatment of an infectious disease includes a step of administering an immune modulator. In some embodiments, the immune modulator promotes the expansion, survival, differentiation, recruitment, or activity of CD4+ or CD8+ T cells.

In some embodiments, the infectious disease is a viral infection. In some embodiments, the infectious disease is a parasite infection. In some embodiments, the infectious disease is a chronic infection.

b. Methods of Detection

In certain embodiments, an in vitro or ex vivo preliminary initial in vivo assay is employed to help identify optimal dosage ranges. Effective doses may be extrapolated from dose response curves derived from in vitro or ex vivo or initial in vivo animal model test systems.

In certain embodiments, the methods of treating cancer disclosed herein comprise the step of identifying a subject with an immune cell or cancer cell sample that has an expression level of an inhibitory checkpoint molecule higher than a predetermined value.

In certain embodiments, the methods disclosed herein directed to treating cancer or determining potential efficacy of β-alethine therapy comprise the step of detecting the expression level of an inhibitory immune checkpoint molecule in an immune cell or cancer cell sample from a subject. In some embodiments, an expression level higher than a predetermined value indicate that the subject is likely to respond favorably to β-alethine therapy. In some embodiments, β-alethine is administered to the subject if the expression level is higher than a predetermined value.

In certain embodiments, the methods disclosed herein directed to treating cancer or determining potential efficacy of β-alethine therapy comprise the step of detecting the expression level of a stimulatory immune checkpoint molecule in an immune cell or cancer cell sample from a subject. In some embodiments, an expression level lower than a predetermined value indicate that the subject is likely to respond favorably to β-alethine therapy. In some embodiments, β-alethine is administered to the subject if the expression level is lower than a predetermined value.

In certain embodiments, the methods disclosed herein determine the efficacy of β-alethine therapy by determining whether ex vivo treatment of an immune cell or cancer cell sample from a subject with β-alethine reduces the expression level of an inhibitory immune checkpoint molecule. In one embodiment, the efficacy of β-alethine therapy is predicted according to the following steps: (i) a sample is isolated from a subject; (ii) the sample is treated with β-alethine; (iii) expression of an inhibitory immune checkpoint molecule is determined, wherein a change of inhibitory checkpoint molecule expression in the sample indicates that the subject is responsive to treatment of β-alethine. In some embodiments, reduced expression of the inhibitory immune checkpoint molecule indicates that the subject is likely to respond favorably to β-alethine therapy. In some embodiments, an effective amount of β-alethine is administered to the subject if the ex vivo treatment of an immune cell or cancer cell sample from the subject with β-alethine reduced expression of the inhibitory immune checkpoint molecule.

In certain embodiments, the methods disclosed herein determine the efficacy of β-alethine therapy by determining whether ex vivo treatment of an immune cell or cancer cell sample from a subject with β-alethine significantly reduces the expression level of a stimulatory immune checkpoint molecule. In one embodiment, the efficacy of β-alethine therapy is predicted according to the following steps: (i) a sample is isolated from a subject; (ii) the sample is treated with β-alethine; (iii) expression of a stimulatory immune checkpoint molecule is determined, wherein a change of stimulatory immune checkpoint molecule expression in the sample indicates that the subject is responsive to treatment of β-alethine. In some embodiments, increased expression of the stimulatory immune checkpoint molecule indicates that the subject is likely to respond favorably to β-alethine therapy. In some embodiments, an effective amount of β-alethine is administered to the subject if the ex vivo treatment of an immune cell or cancer cell sample from the subject with β-alethine increased expression of the stimulatory immune checkpoint molecule.

In some embodiments, the immune cell or cancer cell sample is a human sample. In some embodiments, the immune cell or cancer cell sample is an animal sample. In some embodiments, the immune cell or cancer cell sample is obtained from a cancer, a cancer region, lymph, bone marrow, body fluid, a tumor, or blood. Non-limiting sources of a sample for use in the present invention include solid tissue, biopsy aspirates, ascites, fluidic extracts, blood, plasma, serum, spinal fluid, lymph fluid, the external sections of the skin, respiratory, intestinal, and genitourinary tracts, tears, saliva, milk, tumors, organs, cell cultures and/or cell culture constituents, for example.

In some embodiments, the methods disclosed herein can be used to examine an aspect of expression of an inhibitory checkpoint molecule. In some embodiments, the methods disclosed herein can be used to examine an aspect of expression of or a state of a sample, including, but not limited to, comparing different types of cells or tissues, comparing different developmental stages, and detecting or determining the presence and/or type of disease or abnormality.

Various methods can be used to assay inhibitory checkpoint molecule mRNA expression levels in a biological sample (e.g., a tumor cell sample or a cancer cell sample). Methods for determining mRNA expression levels of an inhibitory checkpoint molecule are known in the art and include, but are not limited to, Northern analysis, nuclease protection assays (NPAs), in situ hybridization, and RT-PCR (e.g., relative quantitative RT-PCR or competitive RT-PCR).

Various methods can also be used to assay the cell surface expression levels of an inhibitory checkpoint molecule in a biological sample (e.g., a tumor cell sample or a cancer cell sample). Methods for determining cell surface expression levels of an inhibitory checkpoint molecule are known in the art and include, but are not limited to, flow cytometry, immunohistological methods, and immunoassays such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I $^{121}$I)) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein, rhodamine, fluorescent proteins, and indirect methods including but not limited to digoxin and biotin. Such labels can be used to label an antibody phage protein, or aptamer. Alternatively, a ligand such as an antibody that recognizes an inhibitory checkpoint molecule described herein can be labeled and used in combination with various analytic and detection procedures known in the art to detect immune modulator levels.

Assaying for the expression level of an inhibitory checkpoint molecule is intended to include qualitatively or quantitatively measuring or estimating the level of an inhibitory checkpoint molecule in a first biological sample either directly (e.g., by determining or estimating mRNA or absolute protein level) or relatively (e.g., by comparing to the disease associated mRNA or protein level to other proteins or nucleic acids). In addition, inhibitory checkpoint molecule expression level in the first biological sample can be measured or estimated and compared to a standard level of an inhibitory checkpoint molecule, the standard being taken from a second biological sample obtained from an individual not having the disease or disorder or being determined by averaging levels from a population of individuals not having a disease or disorder. As will be appreciated in the art, once the "standard" immune modulator level is known, it can be used repeatedly as a standard for comparison.

β-alethine, one or more immune modulators, and/or the compositions disclosed herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular anti-cancer agent (e.g., β-alethine or a chemotherapeutic agent) or an antibody (e.g., an anti-inhibitory checkpoint molecule antibody), including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

In one embodiment, an anti-inhibitory checkpoint molecule antibody can be used in immunohistochemistry of blood, body fluid, biopsy samples or fine needle aspirates, or in vivo imaging.

In another embodiment, an anti-inhibitory checkpoint molecule antibody can be used to detect levels of an inhibitory checkpoint molecule, or levels of cells which contain a specific inhibitory checkpoint molecule on their membrane surface, which levels can then be linked to certain disease symptoms. An anti-inhibitory checkpoint molecule antibody described herein may carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-inhibitory checkpoint molecule antibodies described herein can carry a fluorescence label or a hapten or ligand that allows secondary binding of such a label. Exemplary fluorescence labels include, for example, reactive and conjugated probes, e.g., Aminocoumarin, Fluorescein and Texas red, Alexa Fluor dyes, Cy dyes and DyLight dyes. For example, an anti-OX-40 antibody can carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{121}I$, $^{124}I$, $^{125}I$, $^{131}I$, $^{198}Au$, $^{211}At$, $^{213}Bi$, $^{225}Ac$ and $^{186}Re$. When radioactive labels are used, currently available counting procedures known in the art may be utilized to identify and quantitate the specific binding of an anti-inhibitory checkpoint molecule antibody to an inhibitory checkpoint molecule. In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with anti-inhibitory checkpoint molecule antibody under conditions that allow for the formation of a complex between the antibody and an inhibitory checkpoint molecule. Any complexes formed between the antibody and the inhibitory checkpoint molecule are detected and compared in the sample and the control. In light of the specific binding of the antibodies described herein for an inhibitory checkpoint molecule, the antibodies thereof can be used to specifically detect inhibitory checkpoint molecule expression on the surface of cells. β-alethine, one or more immune modulators, and the compositions disclosed herein described herein can also be used to purify proteins of interest via immunoaffinity purification.

In some aspects, methods for in vitro, ex vivo and detecting an inhibitory checkpoint molecule in a sample, comprising treating an isolated sample with β-alethine and contacting said sample with an anti-inhibitory checkpoint molecule antibody, are provided herein. In some aspects, provided herein is the use of an antibody provided herein, for in vitro and ex vivo detecting an inhibitory checkpoint molecule in a sample. In one aspect, provided herein is an antibody or pharmaceutical composition provided herein for use in the detection of an inhibitory checkpoint molecule disclosed herein in a subject. In one preferred embodiment, inhibitory checkpoint molecule detected is a human inhibitory checkpoint molecule disclosed herein. In one preferred embodiment, the subject is a human.

IV. Kits

Also disclosed herein is a pharmaceutical kit comprising at least two compartments, one compartment comprising β-alethine and another compartment comprising an immune modulator.

The kits disclosed herein comprise one or more pharmaceutical compositions described herein. In a specific embodiment, provided herein is a pharmaceutical pack or kit comprising one or more containers filled with one or more of the ingredients of the pharmaceutical compositions described herein, such as β-alethine, one or more immune modulators provided herein, and/or one or more antibodies provided herein. In some embodiments, the kits contain a pharmaceutical composition described herein and any prophylactic or therapeutic agent, such as those described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises a purified pharmaceutical composition described herein. In a specific embodiment, kits described herein contain one or more compositions that can be used as a control. In another specific embodiment, kits described herein contain one or more elements for detecting the expression of an inhibitory checkpoint molecule disclosed herein. In some embodiments, the inhibitory checkpoint molecule is detected by a detection agent such as a fluorescent compound, an enzymatic substrate, a radioactive compound or a luminescent compound, or an antibody. In specific embodiments, a kit provided herein includes one or more recombinantly produced or chemically synthesized inhibitory checkpoint molecules as a control. The detection agents provided in the kit can also be attached to a solid support.

The present invention provides kits that comprise the pharmaceutical compositions or other agents described herein and that can be used to perform the methods described herein. In some embodiments, the kits contain all of the components necessary and/or sufficient to perform a detection assay, including all controls, directions for performing assays, and any necessary software for analysis and presentation of results.

In some embodiments, the immune modulator of the kit is an antagonist of an inhibitory immune checkpoint molecule. In some embodiments, the immune modulator of the kit inhibits or blocks the activity of an inhibitory immune checkpoint molecule selected from the group consisting of: PD1 (also called PDCD1 or CD279); PD-L1 (also called B7-H1 or CD274); PD-L2 (also called B7-DC or CD273); CTLA-4 (also called CD152); B7-H3 (also called CD276); B7-H4 (also called B7S1 or B7x); CD66a (CEACAM1); VISTA (also called B7-H5 or GI24); BTLA; CD160; LAG3 (also called CD223 or Lymphocyte activation gene 3); Indoleamine 2,3-dioxygenase (also called IDO); Galectin-9 (also called LGALS9); TIM-3 (also called HAVCR2); 2B4 (also called CD244); SIRP alpha (also called CD172a);

CD39; CD47; CD48 (also called SLAMF2); A2AR; KIRs; and TIGIT (also called VSTM3). In some embodiments, the inhibitory immune checkpoint molecule of the kit is PD-1. In some embodiments, the immune modulator of the kit is an antibody, antibody fragment, or ligand that binds to the inhibitory immune checkpoint molecule. In some embodiments, the immune modulator of the kit is an anti-PD-1 antibody or antibody fragment thereof, an anti-PD-L1 antibody or antibody fragment thereof, or an anti-CTLA-4 antibody or antibody fragment thereof.

In some embodiments, the immune modulator of the kit is an agonist of a co-stimulatory immune checkpoint molecule. In some embodiments, the immune modulator of the kit stimulates the activity of an co-stimulatory immune checkpoint molecule selected from the group consisting of: OX-40 (also called CD134); CD226 (also called DNAM-1); CD137 (also called 4-1BB); CD40L (also called CD154 or TNFSF5); 4-1BBL (also called CD137L); OX-40L (also called TNFSF4 or CD252); CD27; TNFSF14 (also called LIGHT or CD258); CD70 (also called CD27L or TNFSF7); CD80 (also called B7-1); CD86 (also called B7-2); GITR (CD357); GITR Ligand (also called TNFSF18); ICOS (CD278); ICOS Ligand (also called B7-H2); HVEM (also called TNFRSF14); DR3; CD28; CD30; CD30L (TNFSF8); TL1A; Nectin-2 (CD112); CD40; CD96; IL-2R (CD122); and CD155 (also called PVR). In some embodiments, the immune modulator of the kit is an antibody, antibody fragment, or ligand that binds to the co-stimulatory immune checkpoint molecule. In some embodiments, the immune modulator of the kit is an agonist of the co-stimulatory immune checkpoint molecule OX-40. In some embodiments, the immune modulator of the kit is an anti-OX-40 antibody or antibody fragment thereof. In some embodiments, the immune modulator of the kit promotes the expansion, survival, differentiation, recruitment, or activity of CD4+ or CD8+ T cells.

EXAMPLES

The following examples are for illustration only. In light of this disclosure, those of skill in the art will recognize that variations of these examples and other examples of the disclosed disclosure be possible without undue experimentation.

Example 1

In Vivo β-Alethine Treatment on Mice with Cloudman Melanomas

Example 1B: Treatment with β-Alethine Alone Simultaneously Down Regulates Checkpoint Inhibitors and Increases CD4+ Cells In Vivo It was hypothesized that β-alethine could affect checkpoint inhibitors expression in vivo in tumor bearing animals. DBA mice were given one subcutaneous injection of 150,000 cells from a Cloudman melanoma cancer cell line, which resulted in palpable tumors in the mice after 10 days. As a baseline, blood from each animal was taken ("Cloudman preBLT"). Mice then were treated with one subcutaneous (s.c.) injection of 30 mg/kg β-alethine. 48 hours after receiving the s.c. injection of β-alethine, blood was taken ("Cloudman postBLT"). The percentage of CD4+ or CD8+ T cells that expressed PD-1, Lag3, or Tim3 was measured at Cloudman preBLT and Cloudman postBLT.

As shown in FIG. 1A, there was a decrease in checkpoint function is illustrated by the reduced percentages of CD4 and CD8 T cells exhibiting the checkpoint inhibitor molecules PD-1, Lag3, and Tim2. In other words, β-alethine simultaneously reduced the percentages of CD4 and CD8 T cells that expressed one of three immune checkpoint molecules in tumor bearing mammals. Thus, by modulating checkpoint inhibitors, β-alethine has a simultaneous and poly or pleiotropic effect on releasing immune inhibition.

As disclosed in Table 1, not only did fewer cells exhibit checkpoint inhibitor molecules, there was a specific reduction in the number of molecule per cell (or mean fluorescent intensity MFI) on cells that continued to have checkpoint molecule expression.

TABLE 1

Checkpoint inhibitor expression (in MFI) in CD4− and CD-8 T Cells.

|  | Pre-β-alethine | Post-β-alethine |
| --- | --- | --- |
| CD4-PD1+ | 273 (±3.5) | 153 (±2.9) |
| CD4-Lag3+ | 74 (±4.5) | 55 (±0.8) |
| CD4-Tim3+ | 112 (±2.5) | 93 (±10) |
| CD8-PD1+ | 345 (±5.3) | 259 (±3.5) |
| CD8-Lag3+ | 540 (±6.7) | 627 (±7.4) |
| CD8-Tim3 | 967 (±10) | 1283 (±7.5) |

In addition, it was observed that the cells that still had some checkpoint inhibitor level had especially high levels of checkpoint inhibitors and may have already been functionally dead or inactive. These results indicate that cells with intermediate levels of checkpoint inhibitors are rescued and activated.

Using the same DBA mice, the percentage of CD4+ T cells, out of all white blood cells, was determined. At 48 hours after treatment with β-alethine, there was a significant increase in the percentage of CD4+ T cells in total white blood cells compared to the samples of the same animals taken just before treatment of β-alethine. FIG. 1B. Thus, a single injection of β-alethine provides a positive effect on the immune system both through the increase in CD4+ white blood cells, a population of cells necessary to provide appropriate T cell help to other immune cells, such as B cells and CD8+ T cells, and via reducing checkpoint inhibition, as shown in Table 2.

TABLE 2

Percentage of white blood cells (WBCs) and WBCs expressing checkpoint inhibitors 48 hours after low dose of β-alethine.

| Cell/CI | Pre- | Post- | Significance |
| --- | --- | --- | --- |
| % CD4+ | 6.4% (±0.8%) | 19.9% (±0.6%) | *p = 0.04 |
| % CD8+ | 1.8% (±0.3%) | 0.9% (±0.6%) | p = 0.08 |
| CD4-PD1 | 8.4% (±0.6%) | 4.4% (±0.9%) | *p = 0.05 |
| CD4-Lag3 | 3.1% (±0.8%) | 2.1% (±0.6%) | p = 0.35 |
| CD4-Tim3 | 2.0% (±0.3%) | 1.3% (±0.3%) | p = 0.1 |
| CD8-PD1 | 6.3% (±0.3%) | 1.2% (±0%) | *p = 0.05 |
| CD8-Lag3 | 1.6% (±0.3%) | 0.1% (±0.03%) | *p = 0.05 |
| CD8-Tim3 | 3.1% (±0.4%) | 0.2% (±0.05%) | *p = 0.05 |

*significance calculated using one-tailed t-test

Example 1B: A Low Dose Subcutaneous Injection of β-Alethine Modulates Immune Response Seven Days after Treatment To examine white blood cell distribution in mice treated with β-alethine, percentage of CD4+ T cells, CD8+ T cells, monocytes, and inflammatory monocytes were determined. DBA mice were given one subcutaneous injection of 150,000 cells from a Cloudman melanoma cancer cell line, which resulted in palpable tumors in the mice. Mice were given either one s.c. injection of a low dose of 30 ng/kg of β-alethine or one s.c. injection of a vehicle control. Seven days after the subcutaneous injection, blood was obtained from both groups.

As shown in FIG. 1C, seven days after a single s.c. injection of 30 ng/kg treatment of β-alethine, mice exhibited a significant increase of the percentages of circulating CD4+ and CD8+ T cells compared to the vehicle control, and a significant decrease of the percentages of circulating monocytes and inflammatory monocytes (which are tumor promoting cells including myeloid derived suppressor cells (MDSCs)) in Cloudman tumor bearing mice compared to the vehicle control. In addition, there was a significant decrease in the percentages of CD4+ T cells that expressed PD-1, Lag3, or Tim3 seven days after β-alethine treatment in Cloudman tumor-bearing mice as well as a significant decrease the percentages of CD8+ T cells that expressed PD-1, Lag3 or Tim3 seven days after β-alethine treatment in Cloudman tumor-bearing mice (data not shown). Thus, a single, low dose injection of β-alethine lead to modulation of the immune system in multiple ways that each contribute to a more active and effective immune system. The relative number of disease fighting CD4 and CD8 cells is increased, further the fraction of those cells that were inactive, as shown by the presence of multiple immune checkpoint molecules, was reduced and further the number of immune suppressive inflammatory macrophages was reduced. In addition, as shown in Table 3, CD4+ and CD8+ T cells are increased after β-alethine treatment. Checkpoint inhibitors such as PD-1, Lag-3, Tim-3 are significantly decreased in CD4+ T cells and Tim-3 is significantly decreased in CD8+ T cells. Finally, total monocytes and percentages of inflammatory monocytes are significantly decreased after treatment with β-alethine. Such changes are linked to effective anti-cancer and anti-infection activity of the immune system.

TABLE 3

Percentage of white blood cells (WBCs) and WBCs expressing checkpoint inhibitors 7 days after low dose of β-alethine.

| Cell/CI | Pre- | Post- | Significance* |
| --- | --- | --- | --- |
| % CD4+ | 11.4% (±0.6%) | 19.6% (±2.7%) | *p = 0.05 |
| % CD8+ | 5.7% (±0.3%) | 7.3% (±0.15%) | *p = 0.05 |
| CD4-PD1 | 13.12% (±1.1%) | 9.1% (± 0.9%) | *p = 0.02 |
| CD4-Lag3 | 3.0% (±0.3%) | 1.94% (±0.3%) | *p = 0.05 |
| CD4-Tim3 | 2.6% (±0.3%) | 1.6% (± 0.2%) | *p = 0.05 |
| CD8-PD1 | 3.2% (±0.14%) | 3.0% (± 0.4%) | p = 0.5 |
| CD8-Lag3 | 2.5% (±0.3%) | 1.8% (± 0.2%) | p = 0.1 |
| CD8-Tim3 | 1.3% (±0.1%) | 1.0% (± 0.06) | *p = 0.05 |
| % Total Monocytes | 11.8% (±0.5%) | 8.8% (± 0.4%) | *p = 0.05 |
| % Inflammatory Monocytes | 4.4% (±0.4%) | 1.2% (± 0.3%) | *p = 0.05 |

*significance calculated using one-tailed t-test

Example 2

Use of β-Alethine to Act Locally Upon a Cancer Micro-Environment

Similar to Example 1, both human patients and animals have received systemic cancer treatment of β-alethine, typically via subcutaneously (s.c.) injections. However, systemic delivery of any molecule could have side effects. Here, it was hypothesized that direct injection into the tumor may be more beneficial to treatment of the tumor, and direct injection may be beneficial in situations where systemic therapy is not successful.

To test this theory, DBA mice were given one subcutaneous injection of 100,000 cells from a Cloudman melanoma cancer cell line, which resulted in palpable tumors in the mice. At 38 days after tumor cell injection, the tumors were 17, 25 and 32 mm². At 38, 46, and 52 days after tumor cell injection, mice were treated with s.c. injections between the shoulder blades (distal to the tumor) of 30 mg/kg β-alethine in sterile saline (each s.c. injection of β-alethine is indicated by triangles in FIG. 2). Tumor size was monitored after each injection. See FIG. 2. At day 56 post-tumor cell injection, one of the mice demonstrated a complete tumor regression. However, the other two mice were then treated with β-alethine at 30 mg/kg intratumorally (i.t.) on day 55 post-tumor cell injection. A second mouse then had complete regression of the tumor seen on day 66 post-tumor cell injection.

The remaining mouse received three more intratumoral injections of 30 mg/kg (β-alethine on days 55, 68, and 82 post-tumor cell injection, and started to demonstrate tumor regression around day 70 post-tumor cell injection. This series of i.t. injections led to a decrease in tumor size and an immediate dramatic reversal of the rapid tumor growth seen before the i.t. injections began. See FIG. 2. These data indicate that i.t. injections of β-alethine have a unique ability to alter cancer growth and presumably the cancer microenvironment via a direct injection. Further, this therapy was not associated with any perceivable local or systemic side effects in the mouse. Thus, it has been demonstrated that application of β-alethine to a tumor via i.t. injection into intact mice reduces tumor size. Further, when β-alethine was injected directly into the tumors, animals that previously had not responded or not fully responded via s.c. injection now responded, included apparent complete response.

Example 3

Example 3A: Delivery of β-Alethine with Anti-PD-1 has a Synergistic Outcome on Tumor Size in DBA Mice As shown in Examples 1 and 2, application of β-alethine to mice in vivo decreased cells expressing checkpoint inhibitors, increased the percentage of CD4+ and CD8+ T cells, decreased suppressor cells and decreased tumor size. Anti-PD-1 antibodies decrease cancer growth (by inhibition of the PD-1 checkpoint). At the time these experiments were done much less was known about the effectiveness of antibodies to reduce other checkpoint molecules such as Tim3 and Lag3. Only those antibodies that interfered with the PD-1 binding (anti PD-1 and anti PDL-1) were known to decrease cancer in patients. Since a predominant action of β-alethine was the reduction of PD-1 it could be hypothesized that administration of antibodies to PD-1 would add little to no benefit.

While checkpoint inhibitors demonstrate effective immune functioning, the majority of patients fail to respond to checkpoint inhibitor therapy, and many patients that initial respond relapse. Thus, methods to enhance the function of checkpoint inhibitors are needed.

In order to evaluate any interaction between anti-PD1 and BA, DBA mice were given one subcutaneous injection of 150,000 cells from a Cloudman melanoma cancer cell line in the flank, which resulted in palpable tumors in the mice by 15 days after the cell line injection. After confirming tumor growth, mice were randomized into the treatment groups listed in Table 4. n=10 mice in the Low Dose, High Dose, q14, untreated, and PBS groups; n=5 mice in PD-1 and BLT/PD-1 groups.

TABLE 4

| Treatment | Description |
| --- | --- |
| Low Dose | s.c. injections of 30 ng/kg β-alethine once a week starting on day 15 |
| High Dose | s.c. injections of 30 mg/kg β-alethine once a week starting on day 15 |
| q14 Dose | s.c. injections of 30 ng/kg β-alethine every 14 days starting on day 15 |
| PD-1 | Intraperitoneal (i.p.) injections of an anti-PD-1 antibody at 50 μg/mouse at days 15, 18, and 21 |
| BLT/PD-1 | s.c. injections of 30 mg/kg β-alethine once a week and i.p. injections of an anti-PD-1 antibody at 50 μg/mouse every 7 days |
| Untreated | No injection |
| PBS | 100 μl s.c. injections every week starting on day 15 |

Tumor growth was measured 3 times a week. As shown in FIG. 3A, the control group, (mice treated with PBS) demonstrated rapid tumor growth. In the PBS treated group, there likely was an artificially low reading in the PBS group on day 23. A repeat reading of tumor size at day 25 confirmed the original trajectory. Treatment with low dose β-alethine alone, high dose β-alethine alone, and anti-PD-1 all delayed tumor growth temporarily, but this effect was not statistically significant. In addition, by day 25, the cancers in all these groups were growing at rates similar to the PBS or untreated control. See FIG. 3A. Remarkably, regardless of the amount of β-alethine that was given (i.e., low dose or high dose), no obvious toxicity was observed in mice in these groups.

The combination treatment group also showed, even more remarkably, no toxicity. Most importantly, beginning at day 18, melanoma growth was completely halted in the BA/PD-1 group, (i.e. only three days after the first injections of β-alethine and anti-PD-1). This lack of tumor growth in the BLT/PD-1 group continued through day 25, and there even was a trend toward decreasing tumor size in this group. So, while neither of the drugs had statistically significant effects as a single agent, the combination of anti-PD-1 and β-alethine completely stopped cancer growth in a potentiating mouse melanoma model: the tumor sizes in this group was significantly different than any of the single agent groups (p<0.0001). Remarkably, each of the 5 mice in the combination treatment group (β-alethine+anti-PD-1) demonstrated complete regression of the tumors. FIG. 3B. The s.c. injections led to a decrease in tumor size to the point that no measureable tumor was detected by 38 days after initial injection of the Cloudman melanoma cell line. Thus, this experiment demonstrates that therapeutic application of β-alethine in combination with a checkpoint therapy such as an anti-PD-1 antibody has a synergistic and unexpected therapeutic effect. It enhances the checkpoint therapies, potentially allowing for greater effectiveness. Further, because the absence of growth of a tumor is a sign of a benign tumor, the combination of β-alethine and a checkpoint inhibitor appears to have the ability to revert malignant growing cancers into benign indolent tumors.

Example 3B: Rescue of Mice with Failed Checkpoint Inhibitor Therapy

As shown in Example 3A, the combination of anti-PD-1 and β-alethine completely halted and even possibly reversed cancer growth in a potentiating mouse melanoma model. In order to further examine this dramatic result, long-term immunity after relapse was determined. In the mice treated with three doses of PD-1 alone at days 15, 18, and 21, tumor size increased through day 29 until the average size was almost 50 mm$^2$. In this group, three mice had some tumor growth and then stable tumor size and two mice had progressive tumor growth. At day 29, mice in the single agent anti-PD-1 treated group received a dose of 30 mg/kg β-alethine subcutaneously, and then weekly thereafter. One of the two mice with progressive tumor growth had complete regression of the tumor after the addition β-alethine therapy as did all mice with stable disease. Even the mouse that had a very large, very fast-growing tumor had a dramatic "partial response"; from day 29 through day 38, the tumor size in this animal decrease over 50%. Thus, in total, 9 of 10 mice in either the combination treatment group or the anti-PD-1 rescued with β-alethine group had complete regression of their tumors. FIG. 4 shows average tumor size in these groups. The group that had received ant-PD1 only, and whose tumors on average were growing at the same rate as controls, had a dramatic reversal in tumor growth upon addition of BA.

In order to determine if these mice had an educated immune system, as further detailed below, all mice with CR were injected with 3 times as many cells as originally required to establish tumors in 15-20 days. At 60 days post challenge only a single mouse had cancer. The one who did not resist re-challenge was the one who took longest to attain CR. Thus 88% of CRs resisted re-challenge and were immune to future tumor challenge.

In these studies, no toxicity was noted in treated animals. This is consistent with previous animal and GLP toxicity studies and the completed human Phase I/II trial. The human trial showed that β-alethine, as a single agent, caused no drug-related adverse events and lead to shrinkage or stabilization in all patients with lymphoma who were not anergic to recall antigens pre-trial.

Here, it is likely that the short course of anti-PD-1, which failed to eliminate the cancer as a single therapy, altered the immune system such that subsequent treatment with β-alethine was effective. After treatment with anti-PD-1, β-alethine therapy was sufficient to cause partial or complete response (no palpable tumor on repeated measurements) in the majority of animals. Statistical comparisons of all animals receiving combination therapy (either concurrently or sequentially) with controls resulted in significant differences using ANOVA for tumor size (p=0.005) or chi-squared tests for tumor presence (p<0.0001).

Example 4

Example 4: β-Alethine Reduces the Percentages of Monocytes Expressing PD-L1 24 Hours after Treatment Given the striking changes in murine immune cells exposed to β-alethine in vivo we hypothesized that the ex vivo application of β-alethine to mammalian cells, including cells of other species, could be used to determine (1) whether β-alethine causes a significant reduction in checkpoint molecules and (2) whether this determines which mammals are good candidates for therapy with β-alethine. In addition, an ex vivo study would identify which mammalian blood cells have excess checkpoint molecules and/or "immune exhaustion" and thus which subjects are good candidates for β-alethine therapy. The antibodies that are checkpoint inhibitors are species specific, thus it was of special interest to see if β-alethine acted across species.

In this study, white blood cells and serum were isolated from three healthy dogs and three dogs with cancer. Two dogs had osteosarcoma (Cancer_1 and Cancer_2 in FIG. 5) and one dog had melanoma (Cancer_3 in FIG. 5). Isolated white blood cells were grown in culture with autologous dog serum and varying doses of β-alethine (0-1000 uM). After 24 hours of incubation with β-alethine, monocytes were isolated and were examined for PD-L1 expression using flow cytometry analysis and a canine-specific anti-PD-L1 antibody. It was observed in some of the dogs that β-alethine reduced the percentages of monocytes expressing PD-L1. Not only does this demonstrate that β-alethine could be used to test a subject's blood ex vivo in order to determine expression of checkpoint inhibitors and ultimately determine whether β-alethine (or a combination of β-alethine and e.g., a checkpoint inhibitor antibody) would be an effective therapy, but also suggests that β-alethine can modulate PD-L1 expression, thus reducing the immune suppressive capabilities of myeloid cells in the tumor microenvironment. Further is documents cross species activity of BA. Current human clinical trials with immune checkpoint inhibitors also include antibodies antagonistic to PD-L1. Thus, β-alethine could also be used synergistically with anti-PD-L1 therapies.

Example 5

Method to Induce Long Term Immunity Using B-Alethine Along with Other Cancer Therapies Example 3 demonstrated that β-alethine decreases growth of cancer especially when used in combination with other immune therapies such as an immune checkpoint inhibitor like an anti-PD-1 antibody. Next, it was determined whether mice already treated with the combination therapy of β-alethine and a checkpoint inhibitor generated an immune response that led to immunity to cancer and resistance to re-challenge with the cancer. Here, DBA mice were given one subcutaneous injection of 150,000 cells from a Cloudman melanoma cancer cell line, which resulted in palpable tumors in the mice by day 14. The experiment described in Example 3 was extended. Specifically, beginning on day 15, mice were given either simultaneous treatment with anti-PD-1 and β-alethine, or sequential treatment of anti-PD-1 beginning on day 15 followed by β-alethine treatment beginning on day 29. In both groups, tumors were seen to stop growing, then shrink and finally not be palpable.

Next, both groups of mice receiving the combination therapy (i.e., with concurrent or delayed treatment of β-alethine) were re-challenged with one subcutaneous injection of 450,000 cells from a Cloudman melanoma cancer cell line, two days after the last β-alethine dose. In only one of 9 cases, the cancer was able to grow. Remarkably, however, 8 of 9 animals demonstrated long term immunity. In these eight animals, no cancer growth was observed even after 4 and 6 weeks after the challenge. Thus, these data demonstrate that β-alethine in combination with an immune checkpoint inhibitor could lead a subject to develop long term immunity against a specific cancer.

Example 6

Combination Treatment of β-Alethine and Immune Modulator in Bladder Cancer Model Next, to test efficacy of individual and combination therapy in a different type of cancer and a different type of mouse and to extend the studies to additional immunomodulators (i.e., antagonists of inhibitory immune checkpoint molecules and agonists of stimulatory immune checkpoint molecules), additional experiments were done in a different lab. CH3 mice were given subcutaneous injections of syngeneic MBT-2 mouse bladder cancer cells at day zero. Mice were randomized based on tumor volume at day 17 and treated with injections of: a monoclonal antibody (mAb) against PD-1 (clone RMP1-14, Rat IgG2a, which was used in the above experiments) following the schedule twice weekly for two weeks, or a mAb against PD-L1 (clone 10F.9G2, Rat IgG2b) at 10 mg/kg/inj (twice weekly for two weeks), or a mAb against CTLA-4 (clone 9H10, Syrian Hamster IgG1) at 10 mg/kg/inj (twice weekly for two weeks), or a mAb against OX-40 at 10 mg/kg/inj (twice weekly for two weeks).

Also beginning at day 17, a subset of mice that received anti-PD-1 and a group that received a no immune modulator received subcutaneous injection of 30 mg/kg of β-alethine once a week for 4 weeks. See FIGS. 6A (survival) and 6B (tumor volume; tumor volume in all parts of FIG. 6 are in mm$^3$). A subset of mice that received anti-PD-L1 (along with a no immune modulator group) received a subcutaneous injection of 600 ng/kg of β-alethine once a week for 4 weeks. See FIG. 6C. Similarly, a subset of mice that received anti-OX-40 (along with a no immune modulator control group) received an subcutaneous injection of 30 mg/kg; 30 μg/kg; or 600 ng/kg of β-alethine once a week for 4 weeks. See FIG. 6D. Finally, a subset of mice that received anti-CTLA-4 (along with no immune modulator control groups) received a subcutaneous injection of 30 μg/kg or 600 ng/kg of β-alethine once a week for 4 weeks. See FIG. 6E. Mice were euthanized if their tumor exceeded 1500 mm$^3$ and the last tumor volume was carried forward for tumor volume graphs and statistics. Mice that died for reasons other than tumor volume were not carried forward. Survival curves show all mice deaths.

The mice treated with the combination of β-alethine and anti-PD-1 had a higher survival rate (FIG. 6A) and lower tumor size (FIG. 6B) compared to PBS-treated animals or anti-PD-1-treated animals. Similarly, mice who received a different immune modulator, anti-PD-L1, in addition to β-alethine, demonstrated lower tumor volume compared to mice treated with PBS or anti-PD-L1 alone (FIG. 6C). In addition, combination treatment of β-alethine with two other immune modulators demonstrated anti-tumor properties. Mice who received a combination treatment of OX-40 with 30 mg/kg of β alethine demonstrated lower tumor volume compared to mice treated with PBS or β-alethine alone. FIG. 6D. And, mice who received a combination treatment of anti-CTLA with 600 ng/kg of β alethine demonstrated lower tumor volume compared to mice treated with PBS or β-alethine alone. FIG. 6E. Thus, these data demonstrate that the combination treatment of β-alethine with different inhibitory or stimulatory immune modulators (including both antagonists of inhibitory immune checkpoint molecules and agonists of stimulatory immune checkpoint molecules) provides antitumoral activity compared to single agent administration.

The invention claimed is:

1. A method of treating cancer in a subject in need thereof, which comprises administering to the subject an effective amount of (1) β-alethine and (2) at least one immune modulator, wherein the at least one immune modulator is an anti-PD-1 antibody or antigen-binding fragment thereof, and wherein the cancer is melanoma or bladder cancer.

2. The method of claim 1, wherein administering β-alethine to the subject comprises subcutaneous administration of β-alethine to the subject.

3. A method of inhibiting tumor growth in a subject having cancer, the method comprising administering an effective amount of β-alethine into the tumor of the subject, wherein the subject has been administered at least one immune modulator, wherein the immune modulator is an anti-PD-1 antibody or antigen-binding fragment thereof, and wherein the cancer is melanoma or bladder cancer.

4. The method of claim 3, wherein β-alethine is injected into the tumor of the subject concurrently with, or after the administration of the at least one immune modulator to the subject.

5. The method of claim 1, wherein the administration of β-alethine occurs concurrently with, or after the administration of the at least one immune modulator.

* * * * *